(12) United States Patent
Ginnebaugh et al.

(10) Patent No.: US 12,201,346 B2
(45) Date of Patent: *Jan. 21, 2025

(54) SURGICAL INSTRUMENT AND METHOD

(71) Applicant: MAQUET CARDIOVASCULAR LLC, Wayne, NJ (US)

(72) Inventors: Fred Ginnebaugh, San Francisco, CA (US); Joseph N. Lamberti, Castro Valley, CA (US); Rohit Girotra, San Francisco, CA (US); Ryan Abbott, San Jose, CA (US); Kenny L. Dang, Laguna Niguel, CA (US); Justin Williams, Oakland, CA (US)

(73) Assignee: Maquet Cardiovascular LLC, Wayne, NJ (US)

( * ) Notice: Subject to any disclaimer, the term of this patent is extended or adjusted under 35 U.S.C. 154(b) by 615 days.

This patent is subject to a terminal disclaimer.

(21) Appl. No.: 17/222,958

(22) Filed: Apr. 5, 2021

(65) Prior Publication Data

US 2021/0220041 A1    Jul. 22, 2021

Related U.S. Application Data

(60) Division of application No. 15/618,112, filed on Jun. 8, 2017, now Pat. No. 10,973,568, which is a division
(Continued)

(51) Int. Cl.
*A61B 18/14* (2006.01)
*A61B 18/08* (2006.01)
*A61B 18/00* (2006.01)

(52) U.S. Cl.
CPC ........ *A61B 18/1445* (2013.01); *A61B 18/085* (2013.01); *A61B 2018/00345* (2013.01);
(Continued)

(58) Field of Classification Search
CPC .............. A61B 18/1445; A61B 18/085; A61B 18/1442; A61B 2018/00345;
(Continued)

(56) References Cited

U.S. PATENT DOCUMENTS 2,137,710 A    11/1938  Anderson
4,031,898 A     6/1977  Hiltebrandt
(Continued)

FOREIGN PATENT DOCUMENTS

AU    2006229913 B2    10/2006
CA       2602015 A1    10/2006
(Continued)

OTHER PUBLICATIONS

PCT International Search Report, PCT/US2006/010569, Jul. 24, 2006, 6 pages.
(Continued)

*Primary Examiner* — Thomas A Giuliani

(57) ABSTRACT

An actuator for use in a surgical instrument, the actuator includes an upper portion configured to be actuated by one or more fingers, wherein the upper portion has an upper distal portion for operating the surgical instrument in a first mode of operation, and an upper proximal portion for operating the surgical instrument in a second mode of operation, and wherein the upper distal portion and the upper proximal portion have different respective tactile configurations for informing the user of the first and second modes of operation, respectively.

18 Claims, 17 Drawing Sheets

Related U.S. Application Data of application No. 15/225,753, filed on Aug. 1, 2016, now abandoned, which is a continuation of application No. 13/094,795, filed on Apr. 26, 2011, now Pat. No. 9,402,680, which is a continuation-in-part of application No. 12/472,657, filed on May 27, 2009, now Pat. No. 9,402,679.

(60) Provisional application No. 61/327,798, filed on Apr. 26, 2010, provisional application No. 61/056,207, filed on May 27, 2008.

(52) U.S. Cl.
CPC .............. *A61B 2018/00404* (2013.01); *A61B 2018/00601* (2013.01); *A61B 2018/0063* (2013.01); *A61B 2018/0091* (2013.01); *A61B 2018/00916* (2013.01); *A61B 2018/1452* (2013.01)

(58) Field of Classification Search
CPC ........... A61B 2018/00404; A61B 2018/00601; A61B 2018/0063; A61B 2018/0091; A61B 2018/00916; A61B 2018/1452; A61B 2018/00607; A61B 2018/00589; A61B 2018/00595; A61B 2018/00958
USPC ........ 606/37, 41, 42, 45, 48–52; 607/98, 99, 607/101, 113, 115, 116
See application file for complete search history.

(56) References Cited

U.S. PATENT DOCUMENTS

| | | |
|---|---|---|
| 4,071,028 A | 1/1978 | Perkins |
| 4,128,099 A | 12/1978 | Bauer |
| 4,281,646 A | 8/1981 | Kinoshita |
| 4,418,692 A | 12/1983 | Guay |
| 4,468,217 A | 8/1984 | Kuzmick |
| 4,759,362 A | 7/1988 | Taniguchi |
| 4,767,519 A | 8/1988 | De Nora |
| 4,801,015 A | 1/1989 | Lubock |
| 4,884,559 A | 12/1989 | Collins |
| 4,884,599 A | 12/1989 | Newman |
| 5,009,661 A | 4/1991 | Michelson |
| 5,052,402 A | 10/1991 | Bencini |
| 5,098,430 A | 3/1992 | Fleenor |
| 5,108,474 A | 4/1992 | Riedy |
| 5,147,356 A | 9/1992 | Bhatta |
| 5,151,102 A | 9/1992 | Kamiyama |
| 5,154,709 A | 10/1992 | Johnson |
| 5,156,613 A | 10/1992 | Sawyer |
| 5,160,334 A | 11/1992 | Billings |
| 5,217,460 A | 6/1993 | Knoepfler |
| 5,258,006 A | 11/1993 | Rydell |
| 5,282,799 A | 2/1994 | Rydell |
| 5,290,278 A | 3/1994 | Anderson |
| 5,300,065 A | 4/1994 | Anderson |
| 5,312,426 A | 5/1994 | Segawa |
| 5,314,424 A | 5/1994 | Nicholas |
| 5,318,040 A | 6/1994 | Kensey |
| 5,336,221 A | 8/1994 | Anderson |
| 5,342,381 A | 8/1994 | Tidemand |
| 5,352,222 A | 10/1994 | Rydell |
| 5,361,583 A | 11/1994 | Huitema |
| 5,364,395 A | 11/1994 | West, Jr. |
| 5,383,888 A | 1/1995 | Zvenyatsky |
| 5,405,344 A | 4/1995 | Williamson |
| 5,443,463 A | 8/1995 | Stern |
| 5,445,638 A | 8/1995 | Rydell |
| 5,451,222 A | 9/1995 | De Maagd |
| 5,453,599 A | 9/1995 | Hall, Jr. |
| 5,462,546 A | 10/1995 | Rydell |
| 5,472,442 A | 12/1995 | Klicek |
| 5,496,317 A | 3/1996 | Goble |
| 5,507,744 A | 4/1996 | Tay |
| 5,507,773 A | 4/1996 | Huitema |
| 5,509,922 A | 4/1996 | Aranyi |
| 5,514,134 A | 5/1996 | Rydell |
| 5,562,503 A | 10/1996 | Ellman |
| 5,599,350 A | 2/1997 | Schulze |
| 5,624,452 A | 4/1997 | Yates |
| 5,647,871 A | 7/1997 | Levine |
| 5,656,408 A | 8/1997 | Silence |
| 5,669,934 A | 9/1997 | Sawyer |
| 5,674,219 A | 10/1997 | Monson |
| 5,683,412 A | 11/1997 | Scarfone |
| 5,709,675 A | 1/1998 | Williams |
| 5,709,680 A | 1/1998 | Yates |
| 5,716,366 A | 2/1998 | Yates |
| 5,722,962 A | 3/1998 | Garcia |
| 5,725,477 A | 3/1998 | Yasui |
| 5,741,285 A | 4/1998 | McBrayer |
| 5,752,973 A | 5/1998 | Kieturakis |
| 5,755,717 A | 5/1998 | Yates |
| 5,766,134 A | 6/1998 | Lisak |
| 5,766,166 A | 6/1998 | Hooven |
| 5,776,130 A | 7/1998 | Buysse |
| 5,807,393 A | 9/1998 | Williamson, IV |
| 5,810,810 A | 9/1998 | Tay |
| 5,810,811 A | 9/1998 | Yates |
| 5,827,271 A | 10/1998 | Buysse |
| 5,833,690 A | 11/1998 | Yates |
| 5,843,017 A | 12/1998 | Yoon |
| 5,849,011 A | 12/1998 | Jones |
| 5,853,410 A | 12/1998 | Greff |
| 5,860,975 A | 1/1999 | Goble |
| 5,871,496 A | 2/1999 | Ginn |
| 5,891,141 A | 4/1999 | Rydell |
| 5,893,835 A | 4/1999 | Witt et al. |
| 5,906,630 A | 5/1999 | Anderhub |
| 5,908,415 A | 6/1999 | Sinofsky |
| 5,908,420 A | 6/1999 | Parins |
| 5,911,719 A | 6/1999 | Eggers |
| 5,944,718 A | 8/1999 | Austin |
| 5,947,984 A | 9/1999 | Whipple |
| 5,954,686 A | 9/1999 | Garito |
| 5,997,533 A | 12/1999 | Kuhns |
| 6,004,320 A | 12/1999 | Casscells |
| 6,022,313 A | 2/2000 | Ginn |
| 6,024,741 A | 2/2000 | Williamson, IV |
| 6,027,501 A | 2/2000 | Goble |
| 6,033,424 A | 3/2000 | Ouchi |
| 6,039,733 A | 3/2000 | Buysse |
| 6,059,781 A | 5/2000 | Yamanashi |
| 6,066,151 A | 5/2000 | Miyawaki |
| 6,074,389 A | 6/2000 | Levine |
| 6,110,190 A | 8/2000 | Ginn |
| 6,113,596 A | 9/2000 | Hooven |
| 6,174,309 B1 | 1/2001 | Wrublewski |
| 6,179,837 B1 | 1/2001 | Hooven |
| 6,190,386 B1 | 2/2001 | Rydell |
| 6,206,876 B1 | 3/2001 | Levine |
| 6,251,092 B1 | 6/2001 | Qin |
| 6,254,623 B1 | 7/2001 | Haibel, Jr. |
| 6,267,761 B1 | 7/2001 | Ryan |
| 6,270,492 B1 | 8/2001 | Sinofsky |
| 6,270,497 B1 | 8/2001 | Sekino |
| 6,273,887 B1 | 8/2001 | Yamauchi |
| 6,352,503 B1 | 3/2002 | Matsui |
| 6,352,532 B1 | 3/2002 | Kramer |
| 6,391,029 B1 | 5/2002 | Hooven |
| 6,406,425 B1 | 6/2002 | Chin |
| 6,406,454 B1 | 6/2002 | Hajianpour |
| 6,423,055 B1 | 7/2002 | Farr |
| 6,432,105 B1 | 8/2002 | Ellman |
| 6,458,122 B1 | 10/2002 | Pozzato |
| 6,464,701 B1 | 10/2002 | Hooven |
| 6,478,794 B1 | 11/2002 | Trapp |
| 6,517,536 B2 | 2/2003 | Hooven |
| 6,521,307 B2 | 2/2003 | Weder |
| 6,522,933 B2 | 2/2003 | Nguyen |
| 6,524,307 B1 | 2/2003 | Palmerton |
| 6,527,771 B1 | 3/2003 | Weadock |

(56) References Cited

U.S. PATENT DOCUMENTS

| | | |
|---|---|---|
| 6,544,210 B1 | 4/2003 | Trudel |
| 6,551,313 B1 | 4/2003 | Levin |
| 6,558,375 B1 | 5/2003 | Sinofsky |
| 6,572,609 B1 | 6/2003 | Farr |
| 6,576,033 B1 | 6/2003 | Booth |
| 6,579,278 B1 | 6/2003 | Bencini |
| 6,579,285 B2 | 6/2003 | Sinofsky |
| 6,582,451 B1 | 6/2003 | Marucci |
| 6,582,536 B2 | 6/2003 | Shimada |
| 6,582,582 B2 | 6/2003 | Becking |
| 6,602,252 B2 | 8/2003 | Mollenauer |
| 6,605,055 B1 | 8/2003 | Sinofsky |
| 6,613,069 B2 | 9/2003 | Boyd |
| 6,626,901 B1 | 9/2003 | Treat |
| 6,652,514 B2 | 11/2003 | Ellman |
| 6,656,177 B2 | 12/2003 | Truckai |
| 6,663,610 B1 | 12/2003 | Thompson |
| 6,676,656 B2 | 1/2004 | Sinofsky |
| 6,679,873 B2 | 1/2004 | Rabiner |
| 6,682,528 B2 | 1/2004 | Frazier |
| 6,685,665 B2 | 2/2004 | Booth |
| 6,695,837 B2 | 2/2004 | Howell |
| 6,702,780 B1 | 3/2004 | Gilboa |
| 6,746,504 B2 | 6/2004 | Booth |
| 6,770,072 B1 | 8/2004 | Truckai |
| 6,773,409 B2 | 8/2004 | Truckai |
| 6,802,843 B2 | 10/2004 | Truckai |
| 6,821,273 B2 | 11/2004 | Mollenauer |
| 6,830,569 B2 | 12/2004 | Thompson |
| 6,860,880 B2 | 3/2005 | Treat |
| 6,908,463 B2 | 6/2005 | Treat |
| 6,958,070 B2 | 10/2005 | Witt |
| 6,966,907 B2 | 11/2005 | Goble |
| 6,966,909 B2 | 11/2005 | Marshall |
| 6,994,707 B2 | 2/2006 | Ellman |
| 7,033,356 B2 | 4/2006 | Latterell |
| 7,083,613 B2 | 8/2006 | Treat |
| 7,083,620 B2 | 8/2006 | Jahns |
| 7,094,231 B1 | 8/2006 | Ellman |
| 7,112,199 B2 | 9/2006 | Cosmescu |
| 7,147,637 B2 | 12/2006 | Goble |
| 7,204,835 B2 | 4/2007 | Latterell |
| 7,211,080 B2 | 5/2007 | Treat |
| 7,306,599 B2 | 12/2007 | Karasawa |
| 7,316,683 B2 | 1/2008 | Kasahara |
| 7,326,202 B2 | 2/2008 | McGaffigan |
| 7,329,257 B2 | 2/2008 | Kanehira |
| 7,364,577 B2 | 4/2008 | Wham |
| 7,367,976 B2 | 5/2008 | Lawes |
| 7,396,356 B2 | 7/2008 | Mollenauer |
| 7,513,896 B2 | 4/2009 | Orszulak |
| 7,632,270 B2 | 12/2009 | Livneh |
| 7,645,289 B2 | 1/2010 | Bayer |
| 7,695,470 B1 | 4/2010 | Stewart |
| 7,699,861 B2 | 4/2010 | Bayer |
| 7,887,558 B2 | 2/2011 | Lin |
| 7,918,845 B2 | 4/2011 | Saadat |
| 7,918,848 B2 | 4/2011 | Lau |
| 8,197,472 B2 | 6/2012 | Lau |
| 8,221,306 B2 | 7/2012 | Okada |
| 8,251,989 B1 | 8/2012 | Newton |
| 8,257,352 B2 | 9/2012 | Lawes |
| 8,425,508 B2 | 4/2013 | Kasahara |
| 8,623,003 B2 | 1/2014 | Lau |
| 8,657,818 B2 | 2/2014 | Lin |
| 8,894,638 B2 | 11/2014 | Lau |
| 8,961,503 B2 | 2/2015 | Lau |
| 9,402,679 B2 | 8/2016 | Ginnebaugh |
| 9,402,680 B2* | 8/2016 | Ginnebaugh ........ A61B 18/085 |
| 9,955,858 B2 | 5/2018 | Pamnani |
| 9,968,396 B2 | 5/2018 | Abbott |
| 2001/0037109 A1 | 11/2001 | Yamauchi |
| 2002/0019631 A1 | 2/2002 | Kidder |
| 2002/0058938 A1 | 5/2002 | Cosmescu |
| 2002/0115997 A1 | 8/2002 | Truckai |
| 2002/0128603 A1 | 9/2002 | Booth |
| 2003/0014052 A1 | 1/2003 | Buysse |
| 2003/0060816 A1 | 3/2003 | Iida |
| 2003/0073991 A1 | 4/2003 | Francischelli |
| 2003/0073994 A1* | 4/2003 | Schulze ............ A61B 18/1445 606/50 |
| 2003/0109876 A1 | 6/2003 | Yamauchi |
| 2003/0125734 A1 | 7/2003 | Mollenauer |
| 2003/0130654 A1 | 7/2003 | Kasahara |
| 2003/0130674 A1 | 7/2003 | Kasahara |
| 2003/0130675 A1 | 7/2003 | Kasahara |
| 2003/0139649 A1 | 7/2003 | Kasahara |
| 2003/0144652 A1 | 7/2003 | Baker |
| 2003/0144660 A1 | 7/2003 | Mollenauer |
| 2003/0163123 A1 | 8/2003 | Goble |
| 2003/0171747 A1 | 9/2003 | Kanehira |
| 2003/0187429 A1 | 10/2003 | Karasawa |
| 2004/0006333 A1 | 1/2004 | Arnold |
| 2004/0054365 A1 | 3/2004 | Goble |
| 2004/0059397 A1 | 3/2004 | Sinofsky |
| 2004/0064151 A1 | 4/2004 | Mollenauer |
| 2004/0068274 A1 | 4/2004 | Hooven |
| 2004/0078035 A1 | 4/2004 | Kanehira |
| 2004/0102450 A1 | 5/2004 | Ewing |
| 2004/0133228 A1 | 7/2004 | Bayer |
| 2004/0176756 A1 | 9/2004 | McGaffigan |
| 2004/0204725 A1 | 10/2004 | Bayer |
| 2004/0260279 A1 | 12/2004 | Goble |
| 2005/0033278 A1 | 2/2005 | McClurken |
| 2005/0049633 A1 | 3/2005 | Watanabe |
| 2005/0070940 A1 | 3/2005 | Genovesi |
| 2005/0072827 A1 | 4/2005 | Mollenauer |
| 2005/0113826 A1 | 5/2005 | Johnson |
| 2005/0113828 A1 | 5/2005 | Shields |
| 2005/0171533 A1 | 8/2005 | Latterell |
| 2005/0182398 A1 | 8/2005 | Paterson |
| 2006/0041254 A1 | 2/2006 | Francischelli |
| 2006/0074444 A1 | 4/2006 | Lin |
| 2006/0211916 A1 | 9/2006 | Kasahara |
| 2006/0217697 A1 | 9/2006 | Lau |
| 2006/0217706 A1* | 9/2006 | Lau ........................ A61B 17/29 606/45 |
| 2006/0235379 A1 | 10/2006 | McClurken |
| 2006/0271037 A1 | 11/2006 | Maroney |
| 2006/0271038 A1 | 11/2006 | Johnson et al. |
| 2007/0021405 A1 | 1/2007 | Abouabdellah |
| 2007/0021424 A1 | 1/2007 | Abouabdellah |
| 2007/0027141 A1 | 2/2007 | Abouabdellah |
| 2007/0078456 A1 | 4/2007 | Dumbauld |
| 2007/0149993 A1 | 6/2007 | Kasahara |
| 2007/0173814 A1 | 7/2007 | Hixson |
| 2007/0213749 A1 | 9/2007 | Kogasaka |
| 2007/0260242 A1 | 11/2007 | Dycus |
| 2007/0293856 A1 | 12/2007 | Paul |
| 2007/0293858 A1 | 12/2007 | Fischer |
| 2008/0015567 A1 | 1/2008 | Kimura |
| 2008/0015575 A1 | 1/2008 | Odom |
| 2008/0039835 A1 | 2/2008 | Johnson |
| 2008/0154091 A1 | 6/2008 | Dejima |
| 2008/0306335 A1 | 12/2008 | Lau |
| 2009/0024121 A1 | 1/2009 | Kasahara |
| 2009/0105539 A1 | 4/2009 | Skerven et al. |
| 2009/0118730 A1 | 5/2009 | Mollenauer |
| 2009/0299367 A1 | 12/2009 | Ginnebaugh |
| 2010/0010310 A1 | 1/2010 | Weisenburgh, II et al. |
| 2010/0048992 A1 | 2/2010 | Okada |
| 2010/0292533 A1 | 11/2010 | Kasahara |
| 2011/0046439 A1 | 2/2011 | Pamnani |
| 2011/0046624 A1 | 2/2011 | Lin |
| 2011/0147853 A1* | 6/2011 | Lin ...................... H01L 23/5256 257/E21.627 |
| 2011/0257643 A1 | 10/2011 | Lau |
| 2011/0288369 A1 | 11/2011 | Ginnebaugh |
| 2011/0288546 A1 | 11/2011 | Abbott |
| 2012/0283720 A1 | 11/2012 | Newton |
| 2012/0316550 A1 | 12/2012 | Lau |
| 2012/0316650 A1 | 12/2012 | Ullrich, Jr. |

(56) References Cited

U.S. PATENT DOCUMENTS

| | | | |
|---|---|---|---|
| 2013/0018373 | A1 | 1/2013 | Lau |
| 2014/0194876 | A1 | 7/2014 | Lau |

FOREIGN PATENT DOCUMENTS

| | | | |
|---|---|---|---|
| CA | 2602381 | A1 | 10/2006 |
| DE | 10328514 | B3 | 3/2005 |
| EP | 0538984 | A2 | 4/1993 |
| EP | 538984 | A3 | 7/1993 |
| EP | 0538984 | B1 | 3/1997 |
| EP | 1330991 | A1 | 7/2003 |
| EP | 1632192 | A1 | 3/2006 |
| EP | 1632192 | B1 | 3/2006 |
| EP | 1330991 | B1 | 9/2007 |
| EP | 1861034 | B1 | 12/2007 |
| EP | 1878399 | A1 | 1/2008 |
| EP | 1878399 | A2 | 1/2008 |
| EP | 1878400 | A1 | 1/2008 |
| EP | 1885270 | B1 | 2/2008 |
| EP | 1894535 | A2 | 3/2008 |
| EP | 2106762 | A1 | 10/2009 |
| EP | 2285305 | A2 | 2/2011 |
| JP | H07508666 | A | 9/1995 |
| JP | H10511030 | A | 10/1998 |
| JP | 2000135222 | A | 5/2000 |
| JP | 2000139943 | A | 5/2000 |
| JP | 2003144451 | A | 5/2003 |
| JP | 2005058553 | A | 3/2005 |
| JP | 2005514102 | A | 5/2005 |
| JP | 4966959 | B2 | 8/2008 |
| JP | 2008534068 | A | 8/2008 |
| JP | 2008534069 | A | 8/2008 |
| JP | 2011521723 | A | 7/2011 |
| WO | 1993020769 | A1 | 10/1993 |
| WO | 1997005829 | A1 | 2/1997 |
| WO | 1997010764 | A1 | 3/1997 |
| WO | 2000047124 | A1 | 8/2000 |
| WO | 2002080794 | A1 | 10/2002 |
| WO | 2003057058 | A1 | 7/2003 |
| WO | 2003061456 | A2 | 7/2003 |
| WO | 2005048863 | A1 | 6/2005 |
| WO | 2006104835 | A1 | 10/2006 |
| WO | 2006104836 | A2 | 10/2006 |
| WO | 2006104836 | A3 | 10/2006 |
| WO | 2009039179 | A1 | 3/2009 |
| WO | 2009154976 | A2 | 12/2009 |
| WO | 2009154976 | A4 | 12/2009 |
| WO | 2009154976 | A9 | 12/2009 |

OTHER PUBLICATIONS

PCT International Preliminary Report on Patentability, PCT/US2006/010569, issued Sep. 25, 2007 and mailed on Oct. 4, 2007, 10 pages.
PCT International Search Report, PCT/US2006/010568, Jul. 24, 2006, 3 pages.
PCT International Preliminary Report on Patentability, PCT/US2006/010568, dated Sep. 25, 2007, 6 pages.
European Examination Report, EP 06739388.4, mailed Sep. 17, 2008, 7 pages.
European Examination Report, EP Application No. EP 06739387.6, Dec. 11, 2008 (4 pages).
Stedman's Medical Dictionary, pp. 3 and 238 (1982), Williams & Wilkins, Baltimore, MD, US.
Non-Final Office Action dated May 7, 2012 for U.S. Appl. No. 12/472,657; (22 pages).
Non-Final Office Action dated Mar. 14, 2012 for U.S. Appl. No. 13/094,783; (8 pages).
Dielectric Heating, downloaded Dec. 2, 2014 from http://www.comdel.com/dielectric-heating, 2 pages.
Electrosurgery: the newest energy-based devices downloaded Dec. 3, 2014 from http://contemporary.obgyn.modernmedicine.com/contemporary-obgyn/cantent/tags/aescula . . . , 6 pages.
Final Office Action Issued in U.S. Appl. No. 15/618,112 mailed on Jun. 29, 2020, 10 pages.
How RF Heating Works, downloaded Dec. 2, 2014 from http://www.macrowave.com/rftech.html, 1 page.
Joule heating, Wikipedia, downloaded Dec. 1, 2014 from http://en.wikipedia.org/wiki/Joule_heating, 6 pages.
L.S. Feldman et al. (eds.), Fundamentals of Electrosurgery Part I: Principles of Radiofrequency Energy for Surgery, the SAGES Manual on the Fundamental Use of Surgical Energy (FUSE), 2012, 15-59, Springer-Verlag, New York.
Ohanian, Hans C, Physics, 1985, 658-660, W.W. Norton & Company, Inc., New York.
PCT International Search Report and Written Opinion, PCT/US2006/010568, dated Aug. 3, 2006, 8 pages.
PCT International Search Report and Written Opinion, PCT/US2006/010569, dated Jan. 4, 2007, 6 pages.
Non-Final Office Action issued in U.S. Appl. No. 15/958,447 mailed on Sep. 2, 2020, 8 pages.
Non-Final Office Action Issued in U.S. Appl. No. 15/618,112 mailed on Nov. 26, 2019, 11 pages.
Non-Final Office Action Issued in U.S. Appl. No. 15/225,753 mailed on Feb. 8, 2017, 7 pages.
Non-Final Office Action Issued in U.S. Appl. No. 13/094,795 mailed on Sep. 29, 2014, 13 pages.
Final Office Action Issued in U.S. Appl. No. 13/094,795 mailed on Apr. 2, 2015, 13 pages.
Non-Final Office Action Issued in U.S. Appl. No. 15/432,699 mailed on May 16, 2019, 6 pages.
Non-Final Office Action Issued in U.S. Appl. No. 14/629,423 mailed on Mar. 15, 2016, 6 pages.
Non-Final Office Action Issued in U.S. Appl. No. 14/148,671 mailed on May 9, 2014, 5 pages.
Non-Final Office Action Issued in U.S. Appl. No. 13/549,367 mailed on Nov. 26, 2012, 6 pages.
Final Office Action Issued in U.S. Appl. No. 13/549,367 mailed on Aug. 9, 2013, 5 pages.
Final Office Action Issued in U.S. Appl. No. 13/549,367 mailed on May 2, 2013, 6 pages.
Final Office Action Issued in U.S. Appl. No. 13/047,778 mailed on Apr. 13, 2012, 6 pages.
Non-Final Office Action Issued in U.S. Appl. No. 11/090,330 mailed on Mar. 22, 2010, 6 pages.
Non-Final Office Action Issued in U.S. Appl. No. 11/090,330 mailed on Nov. 17, 2009, 6 pages.
Non-Final Office Action Issued in U.S. Appl. No. 11/090,330 mailed on Jan. 29, 2009, 5 pages.
Non-Final Office Action Issued in U.S. Appl. No. 11/090,330 mailed on Apr. 2, 2008, 13 pages.
Final Office Action Issued in U.S. Appl. No. 11/090,330 mailed on Aug. 6, 2010, 5 pages.
Final Office Action Issued in U.S. Appl. No. 11/090,330 mailed on May 15, 2009, 5 pages.
Non-Final Office Action Issued in U.S. Appl. No. 11/090,750 mailed on May 16, 2011, 8 pages.
Non-Final Office Action Issued in U.S. Appl. No. 11/090,750 mailed on Dec. 28, 2010, 5 pages.
Non-Final Office Action Issued in U.S. Appl. No. 11/090,750 mailed on Feb. 22, 2010, 9 pages.
Non-Final Office Action Issued in U.S. Appl. No. 11/090,750 mailed on Nov. 10, 2008, 13 pages.
Final Office Action Issued in U.S. Appl. No. 11/090,750 mailed on Apr. 2, 2008, 10 pages.
Final Office Action Issued in U.S. Appl. No. 11/090,750 mailed on Apr. 17, 2009, 9 pages.
Non-Final Office Action Issued in U.S. Appl. No. 13/494,985 mailed on Dec. 23, 2013, 7 pages.
Non-Final Office Action Issued in U.S. Appl. No. 13/494,985 mailed on May 17, 2013, 7 pages.
Final Office Action Issued in U.S. Appl. No. 13/494,985 mailed on Aug. 26, 2013, 7 pages.
Final Office Action Issued in U.S. Appl. No. 13/494,985 mailed on Sep. 19, 2012, 6 pages.

(56) References Cited

OTHER PUBLICATIONS

Non-Final Office Action Issued in U.S. Appl. No. 14/551,599 mailed on Feb. 4, 2016, 9 pages.
Final Office Action Issued in U.S. Appl. No. 14/551,599 mailed on May 26, 2016, 9 pages.
Non-Final Office Action Issued in U.S. Appl. No. 15/482,310 mailed on Jan. 8, 2020, 4 pages.
Final Office Action issued in U.S. Appl. No. 15/961,676 on Apr. 20, 2021.
Non-Final Office Action Issued in U.S. Appl. No. 12/545,690 mailed on Nov. 5, 2015, 14 pages.
Non-Final Office Action Issued in U.S. Appl. No. 12/545,690 mailed on Apr. 28, 2014, 22 pages.
Non-Final Office Action Issued in U.S. Appl. No. 12/545,690 mailed on Jan. 8, 2013, 12 pages.
Final Office Action Issued in U.S. Appl. No. 12/545,690 mailed on Jul. 14, 2016, 20 pages.
Final Office Action Issued in U.S. Appl. No. 12/545,690 mailed on Dec. 15, 2014, 32 pages.
Final Office Action Issued in U.S. Appl. No. 12/545,690 mailed on Oct. 21, 2013, 15 pages.
Non-Final Office Action Issued in U.S. Appl. No. 12/472,657 mailed on Jun. 3, 2014, 19 pages.
Non-Final Office Action Issued in U.S. Appl. No. 12/472,657 mailed on May 7, 2012, 13 pages.
Final Office Action Issued in U.S. Appl. No. 12/472,657 mailed on Feb. 4, 2015, 17 pages.
Final Office Action Issued in U.S. Appl. No. 12/472,657 mailed on Jan. 14, 2013, 17 pages.
Final Office Action issued in U.S. Appl. No. 11/090,750, mailed Jun. 11, 2010, 11 pages.
Ex Parte Quayle Action issued in U.S. Appl. No. 11/090,750, mailed Sep. 6, 2011, 4 pages.
Final Office Action issued in U.S. Appl. No. 13/494,985, mailed Sep. 19, 2012, 7 pages.
Final Office Action issued in U.S. Appl. No. 13/094,783, mailed Aug. 30, 2012, 12 pages.
International Preliminary Report on Patentability issued in International Application No. PCT/US2009/045272 on Nov. 30, 2010, 11 pages.
Office Action issued in U.S. Appl. No. 13/094,783 on Jul. 31, 2014, 16 pages.
Final Office Action issued in U.S. Appl. No. 13/094,783 on Apr. 29, 2015, 17 pages.
Office Action issued in JP Application No. 2012-209125 on Oct. 15, 2013, 6 pages.
Office Action issued in EP Application No. 09767288.5 on Jun. 24, 2015, 4 pages.
Office Action issued in U.S. Appl. No. 13/094,783 on Dec. 7, 2015, 18 pages.
Office Action issued in EP Application No. 09767288.5 on Apr. 14, 2016, 3 pages.
Final Office Action issued in U.S. Appl. No. 13/094,783 on Aug. 1, 2016, 18 pages.
Office Action issued in U.S. Appl. No. 13/094,783 on Mar. 16, 2017, 18 pages.
Extended European Search Report issued in EP Application No. 16002268.7 on Apr. 21, 2017, 7 pages.
Office Action issued in U.S. Appl. No. 15/961,676 on Oct. 30, 2020, 10 pages.
Final Office Action issued in U.S. Appl. No. 15/958,447 on Jan. 12, 2021, (9 pages).
Non-Final Office Action issued in U.S. Appl. No. 15/958,447 on Aug. 16, 2021, 10 pages.
Non-Final Office Action issued in U.S. Appl. No. 15/961,676 on Oct. 13, 2021, 10 pages.
Final Office Action issued in U.S. Appl. No. 15/961,676 on May 27, 2022, 9 pages.
Non-Final Office Action Issued in U.S. Appl. No. 15/961,676 mailed on Nov. 16, 2022, 9 pages.
Non-Final Office Action issued in U.S. Appl. No. 17/820,430 mailed on May 19, 2023, 7 pages.
Non-Final Office Action Issued in U.S. Appl. No. 17/068,666 mailed on Jan. 9, 2024, 9 pages.
Final Office Action Issued in U.S. Appl. No. 17/820,430 mailed on Feb. 22, 2024, 7 pages.

\* cited by examiner

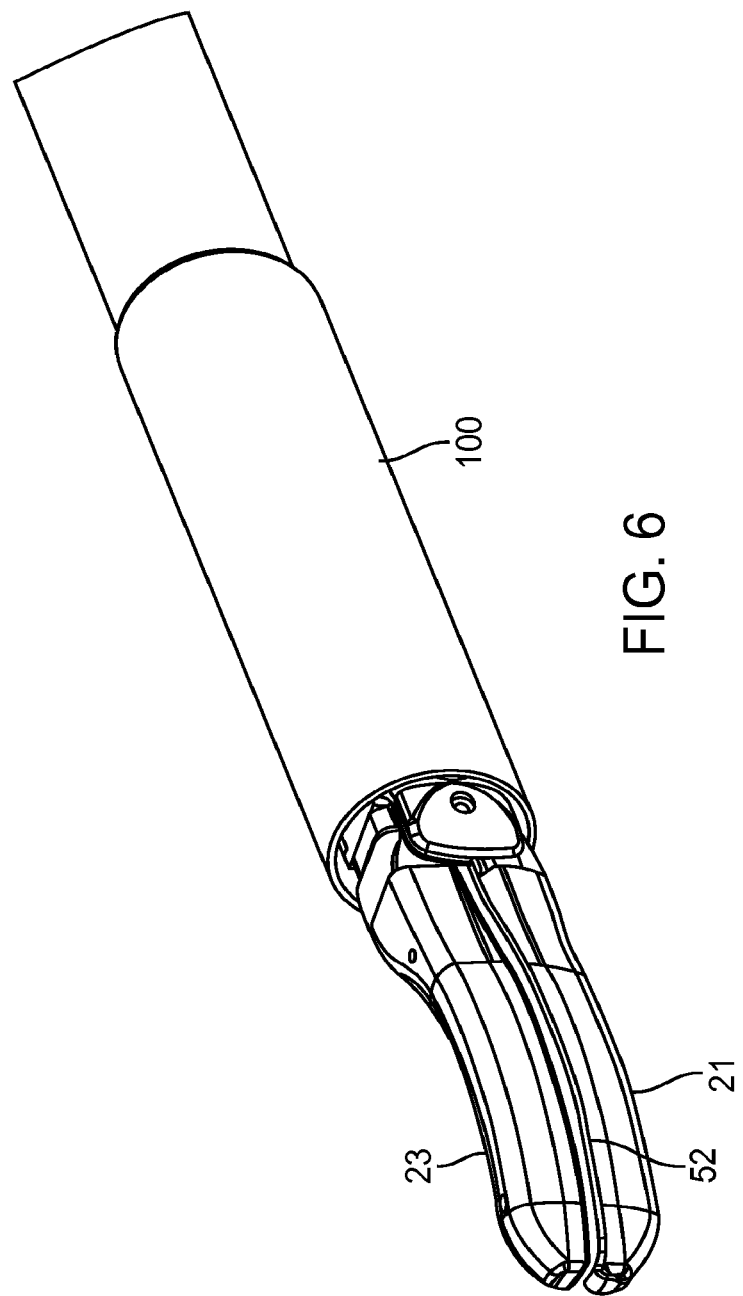

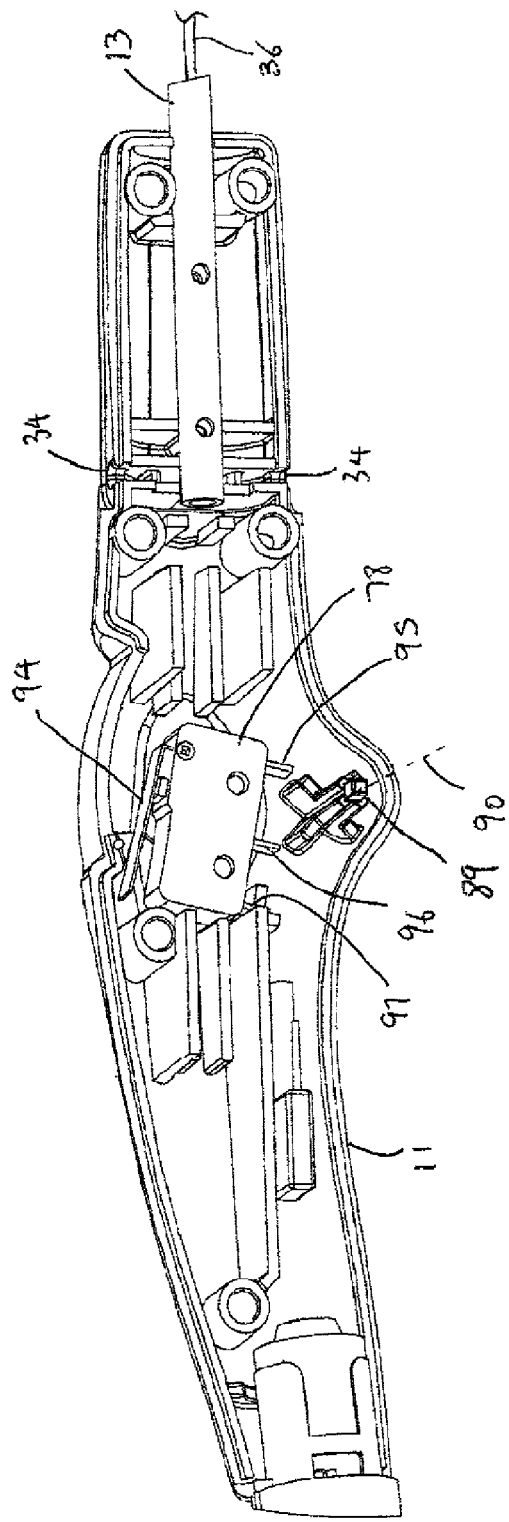

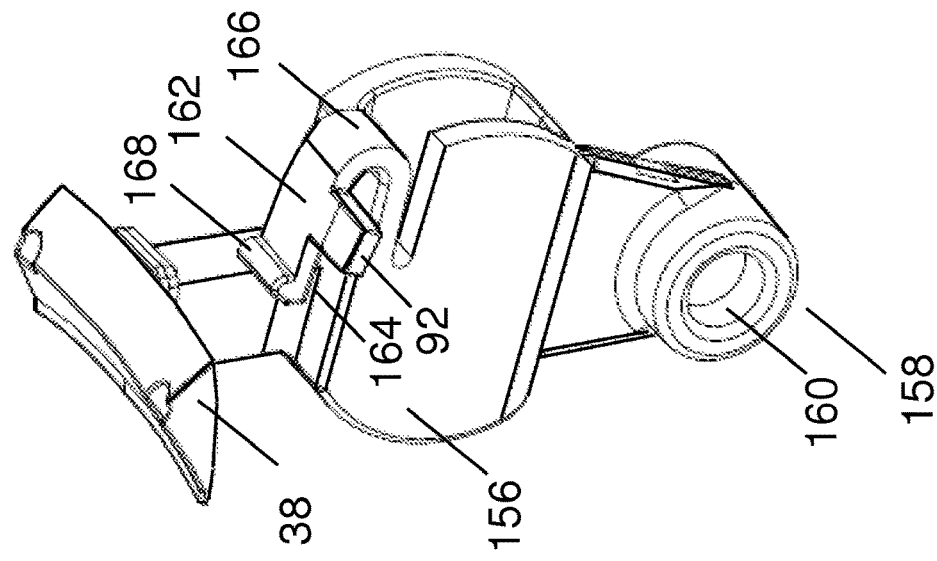
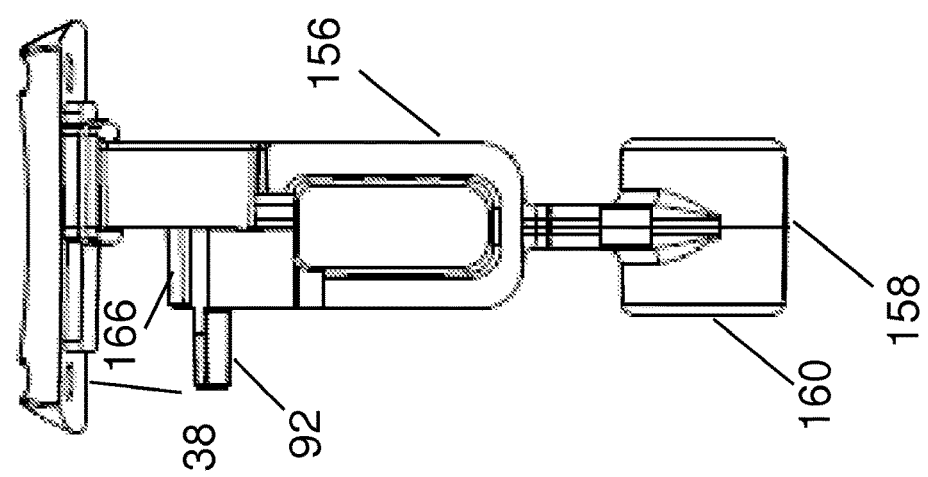
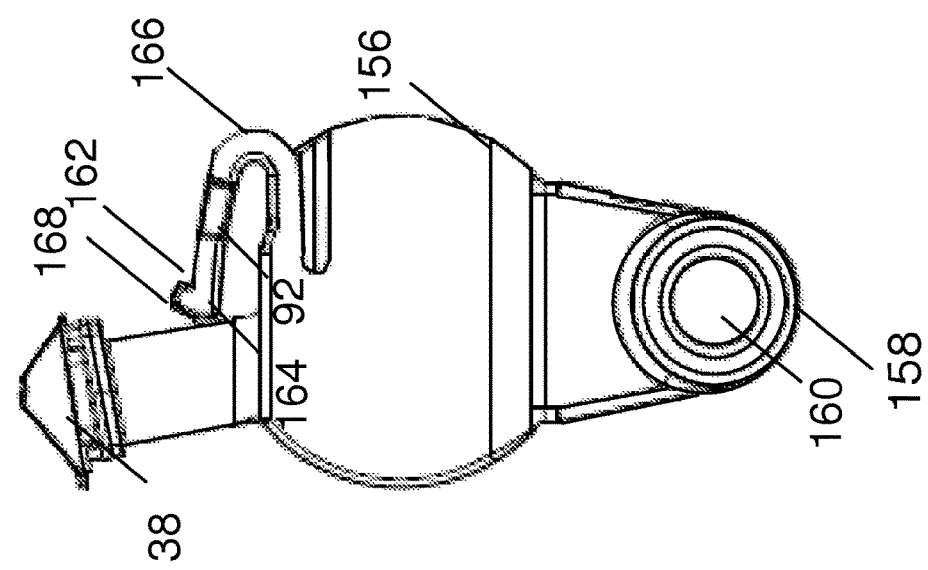
FIG. 9D
FIG. 9C
FIG. 9B

SURGICAL INSTRUMENT AND METHOD

RELATED APPLICATION DATA

This application is a divisional of U.S. patent application Ser. No. 15/618,112, filed Jun. 8, 2017 (now U.S. Pat. No. 10,973,568), which is a divisional of U.S. patent application Ser. No. 15/225,753, filed Aug. 1, 2016 (now abandoned), which is a continuation of U.S. patent application Ser. No. 13/094,795, filed Apr. 26, 2011 (now U.S. Pat. No. 9,402,680), which claims the benefit of priority to U.S. provisional patent application Ser. No. 61/327,798, filed Apr. 26, 2010, and which is a continuation-in-part of U.S. patent application Ser. No. 12/472,657, filed on May 27, 2009 (now U.S. Pat. No. 9,402,679), which claims the benefit of priority to U.S. provisional patent application Ser. No. 61/056,207, filed on May 27, 2008. The entire disclosures of all of the applications identified in this paragraph are expressly incorporated by reference herein.

FIELD

This application relates to a surgical instrument, and more particularly, to a vessel harvesting device.

BACKGROUND

In endoscopic vessel harvesting (EVH) surgical procedures, a long slender surgical instrument may be advanced into a tunnel next to the saphenous vein in a patient's leg, and along the saphenous vein to dissect the vessel away from adjacent tissue, and to sever side-branch vessels along the course of the vessel to be harvested. Similar technique may also be used to harvest a radial artery or other target structure.

A vessel harvesting device often includes a surgical tool at the distal end of the harvesting device, and a handle with a control for operating the surgical tool. Controls typically have a symmetrical configuration and are unintuitive.

SUMMARY

In accordance with some embodiments, a surgical instrument for harvesting a vessel includes a handle at the proximal end of the surgical instrument, and an actuator moveably coupled to the handle for operating the surgical instrument, an upper portion of the actuator configured to be actuated by one or more fingers, wherein the upper portion has an upper distal portion for operating the surgical instrument in a first mode of operation, and an upper proximal portion for operating the surgical instrument in a second mode of operation, and wherein the upper distal portion and the upper proximal portion have different respective tactile configurations for informing the user of the first and second modes of operation, respectively.

In accordance with other embodiments, an actuator for use in a surgical instrument, the actuator includes an upper portion configured to be actuated by one or more fingers, wherein the upper portion has an upper distal portion for operating the surgical instrument in a first mode of operation, and an upper proximal portion for operating the surgical instrument in a second mode of operation, and wherein the upper distal portion and the upper proximal portion have different respective tactile configurations for informing the user of the first and second modes of operation, respectively.

In accordance with some embodiments, a surgical instrument for harvesting a vessel includes an elongated body having a distal end and a proximal end, a surgical device at the distal end of the elongated body, wherein the surgical device is configured to operate on a vessel, a handle at the proximal end of the elongated body, and a control moveably coupled to the handle for operating the surgical device, the control configured to be actuated by one or more fingers, wherein the control has a distal portion for operating the surgical device in a first mode of operation, and a proximal portion for operating the surgical device in a second mode of operation, and wherein the distal portion and the proximal portion have different respective configurations for informing the user of the first and second modes of operation, respectively.

In other embodiments, the distal portion of the control has a concave configuration, and the proximal portion of the control has a convex configuration.

In other embodiments, wherein the distal portion of the control has a first resistance to motion, and the proximal portion of the control has a second resistance to motion that is different from the first resistance to motion.

In other embodiments, the surgical device comprises a jaw assembly having a first jaw member and a second jaw member, and the control is moveable for opening and closing the jaw assembly.

In other embodiments, the jaw assembly further includes an electrode, and the control is moveable for controlling a delivery of energy to the electrode.

In other embodiments, the surgical device is configured for sealing and cutting the vessel.

In other embodiments, the surgical instrument further includes a cable coupled to the handle, wherein the surgical device comprises an electrode, and wherein the cable has a first wire and a second wire that are electrically coupled to a fuse that connects to the electrode, the second wire being a backup wire for supplying energy to the fuse.

In other embodiments, the surgical instrument further includes an electrical switch within the handle, wherein the handle has two wires that are electrically coupled to a switch terminal at the electrical switch, with one of the two wires being a backup wire for supplying energy to the switch terminal.

In other embodiments, the surgical instrument further includes an electrical switch within the handle, wherein the control has a first portion located inside the handle for pressing a lever at the electrical switch, and a second portion for providing a tactile feedback to a user of the surgical instrument when the lever at the electrical switch has been pressed.

In accordance with some embodiments, a surgical instrument for harvesting a vessel includes an elongated body having a distal end and a proximal end, a surgical device at the distal end of the body, the surgical device configured to operate on a vessel, and having an electrode, a handle coupled to the proximal end of the elongated body, an electrical switch for activating the electrode, and a control moveably mounted on the handle, wherein the control comprises a first portion for actuating the electrical switch, and a second portion for providing a tactile feedback to a user of the surgical instrument when the electrical switch has been actuated, and wherein the first and the second portions of the control have an unity construction.

In other embodiments, the first portion of the control is configured for pressing a lever at the electrical switch in response to a movement of the control.

In other embodiments, the control is asymmetric such that a distal portion of the control and a proximal portion of the control have different respective configurations.

In other embodiments, the distal portion of the control has a concave configuration, and the proximal portion of the control has a convex configuration.

In other embodiments, the distal portion of the control has a first resistance to motion, and the proximal portion of the control has a second resistance to motion that is different from the first resistance to motion.

In other embodiments, the surgical device further comprises a jaw assembly having a first jaw member and a second jaw member, and the control is moveable for opening and closing the jaw assembly.

In other embodiments, the surgical device is configured for sealing and cutting the vessel.

In other embodiments, the surgical instrument further includes a cable coupled to the handle, wherein the cable has a first wire and a second wire that are electrically coupled to the electrode, the second wire being a backup wire for supplying energy to the electrode.

In other embodiments, the cable has two wires that are electrically coupled to a switch terminal at the electrical switch, with one of the two wires being a backup wire for supplying energy to the switch terminal.

In accordance with some embodiments, a surgical instrument for harvesting a vessel includes an elongated body having a distal end and a proximal end, an electrical circuit, a surgical device at the distal end of the body, wherein the surgical device comprises an electrode coupled to the electrical circuit, and a handle coupled to the proximal end of the elongated body, wherein the electrical circuit has a first wire and a second wire that are parts of a circuit coupled to the electrode, the second wire being a backup wire.

In other embodiments, the first and second wires are electrically connected to the electrode, the second wire being a backup wire for supplying energy to the electrode.

In other embodiments, the surgical instrument further includes a fuse that couples to the electrode, wherein the first wire and the second wire are electrically coupled to the fuse, the second wire being a backup wire for supplying energy to the fuse.

In other embodiments, the surgical instrument further includes an electrical switch within the handle, wherein the first wire and the second wire are electrically coupled to a switch terminal at the electrical switch, the second wire being a backup wire for supplying energy to the switch terminal.

In other embodiments, the surgical instrument further includes a control moveably mounted on the handle for operating the surgical device, wherein the control is asymmetric such that a distal portion of the control and a proximal portion of the control have different respective configurations.

In other embodiments, the distal portion of the control has a concave configuration, and the proximal portion of the control has a convex configuration.

In other embodiments, the distal portion of the control has a first resistance to motion, and the proximal portion of the control has a second resistance to motion that is different from the first resistance to motion.

In other embodiments, the surgical device is configured for sealing and cutting the vessel.

In other embodiments, the surgical instrument further includes an electrical switch within the handle, wherein the control has a first portion for pressing a lever at the electrical switch, and a second portion for providing a tactile feedback to a user of the surgical instrument.

In other embodiments, the first and second portions of the control have a unity construction.

Other and further aspects and features will be evident from reading the following detailed description of the embodiments, which are not intended to limit the invention.

BRIEF DESCRIPTIONS OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

FIG. 6 is a partial perspective view of a pair of jaws at a distal end of a surgical instrument, wherein the jaws are being operated as a monopolar electrode in accordance with some embodiments;

FIGS. 7A and 7B are partial views of a handle showing its internal operational mechanisms at a proximal end of a surgical instrument in accordance with some embodiments;

FIGS. 9A-9G illustrates different views of the actuator components of the handle of FIG. 1 in accordance with some embodiments; FIG. 9A illustrates the actuator assembly;

FIGS. 9B-9D illustrate different views of the actuator subcomponent without the over-molded piece; FIGS. 9E-9G illustrate different views of the over-molded piece on the button of the actuator;

DETAILED DESCRIPTION

Figure 1:
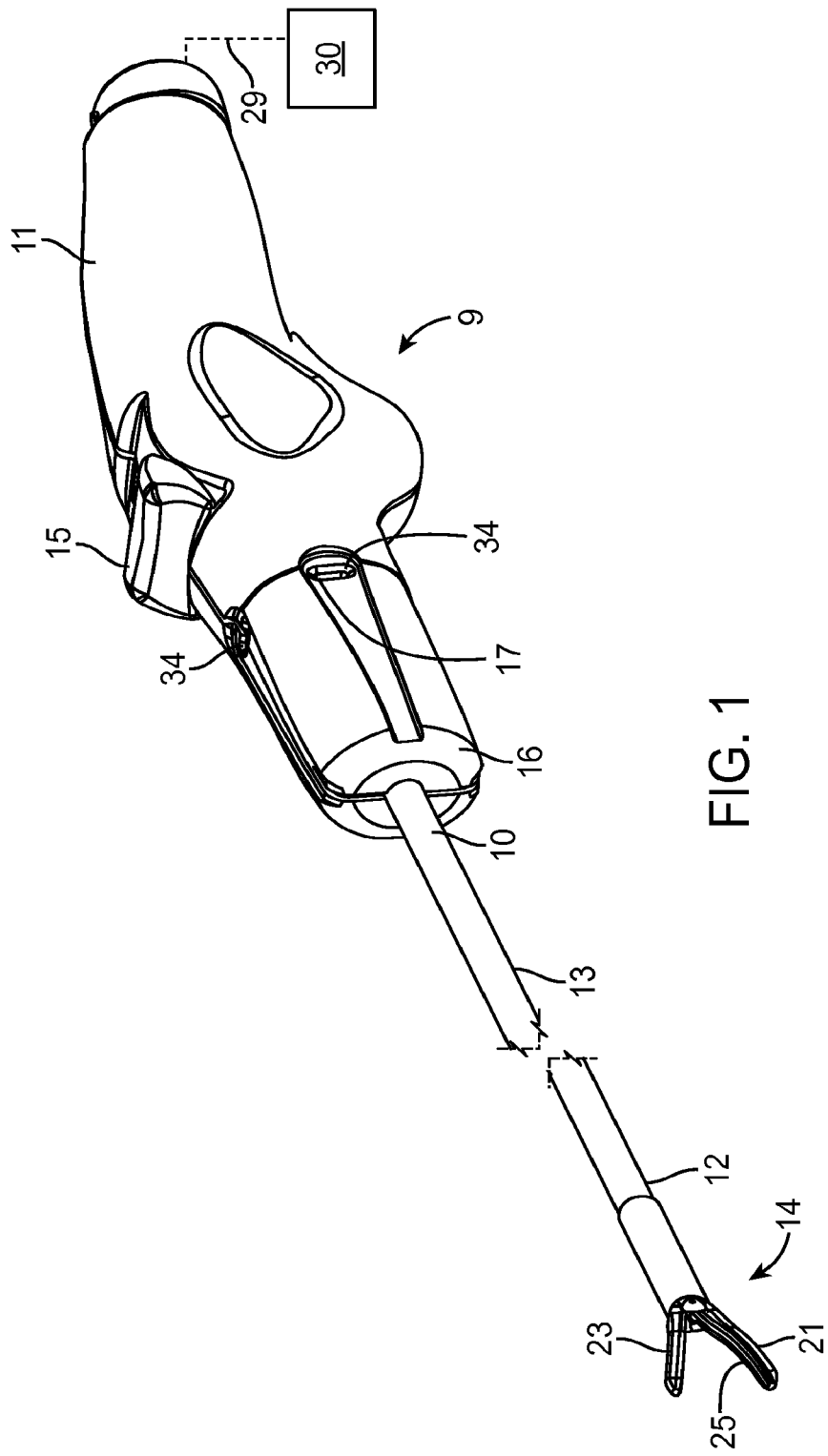
FIG. 1 illustrates a surgical instrument in accordance with some embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

Symmetrical control configurations often make using related art devices unintuitive. For example, such controls may be moveable in a proximal direction to activate an electrode at the surgical tool, and may be moveable in a distal direction to deactivate the electrode. If the control is symmetric with respect to the directions of operation, then a user may become confused as to whether he/she is activating or deactivating the electrode. The exemplary embodiments help to make a control more intuitive.

FIG. 1 illustrates a surgical instrument 9 in accordance with some embodiments. The surgical instrument 9 includes a handle 11, an elongated body 13 having a proximal end 10 and a distal end 12, and a surgical device/tool 14 located at the distal end 12 of the body 13. The proximal end 10 of the elongated body 13 is coupled to a distal end 16 of the handle 11. As used in this specification, the term "surgical device" refers to any device or component that may be used to operate on tissue (e.g., to treat, manipulate, handle, hold, cut, heat, or energize, etc., tissue). The elongated body 13 may be rigid, or alternatively, flexible. The handle 11 includes an actuator 15 that is coupled to the surgical device 14 through a linkage (not shown) within a bore of the elongated body 13 for controlling an operation of the surgical device 14. The handle 11 and the actuator 15 may be made from insulative material(s) such as plastic.

In the illustrated embodiments, the surgical device 14 includes a pair of jaws 21, 23 for clamping, cutting, and sealing a vessel. The jaw 21 includes an electrically conductive material 25 which faces towards the opposing jaw 23. Alternatively, or additionally, the jaw 23 may include an electrically conductive material which faces towards jaw 21. The electrically conductive material 25 is in a form of an electrode, and is configured to selectively provide heat or RF energy during use. As used in this specification, the term "electrode" refers to a component that is for delivering energy, such as heat energy, RF energy, etc., and thus, should not be limited to a component that delivers any particular form of energy. The electrically conductive material 25 may be Ni-chrome, stainless steel, or other metals or alloys in different embodiments. The jaws 21, 23 are configured to close in response to actuation (e.g., pressing, pulling, or pushing, etc.) of the actuator 15, thereby clamping a vessel during use. In the illustrated embodiments, the actuator 15 may be further actuated (e.g., further pressed, further pulled, or further pushed, etc.) to cause the electrically conductive material 25 to provide (e.g., emit) heat, thereby cutting and sealing the clamped vessel. In particular, when the actuator is further actuated, the electrically conductive material 25 is electrically coupled, via a cable 29, to a DC source 30, which provides a current to the electrically conductive material (electrode) 25, thereby heating the electrode 25. After the vessel is cut and sealed, the actuator 15 may be de-actuated to stop the delivery of current to the electrode 25, and may be further de-actuated to open the jaws 21, 23. The mechanical linkage for translating operation of the actuator 15 into closing and opening of the jaws 21, 23 may be implemented using cables, shafts, gears, or any of other mechanical devices that are known in the art. In other embodiments, the source 30 may be other types of energy source, and need not be a DC source.

In the illustrated embodiments, the handle 11 also includes a plurality of electrical contact terminals 17 in respective ports 34 near the distal end 16 of the handle 11. The contact terminals 17 are electrically coupled to the electrically conductive material 25 at the surgical device 14, and are configured (e.g., shaped, sized, and positioned) for receiving RF energy from a RF source. In some embodiments, each contact terminal 17 is electrically connected to the electrode 25 via electrical line that may be housed within a wall of the elongated body 13, or that may be in a form of a cable that is housed within the bore of the elongated body 13. In some embodiments, the elongated body 13 may include an outer layer of bioinert electrically insulative material. In other embodiments, instead of being located inside the port 34, the contact 17 may be in a form of a ring located and exposed near the distal end 16 of the handle 11.

The linkage that mechanically couples the jaws 21, 23 to the actuator 15 may be electrically insulated, for example, by silicone rubber, ceramic or other suitable non-electrically conductive material. This assures that high frequency energy supplied to the contact region 17 is conducted along the electric line housed by the body 13 to the electrically conductive material (electrode) 25 at jaw 21 (and/or electrode at jaw 23). In other embodiments, the body 13 may not include an electric line for coupling the contact region 17 to the electrode 25. Instead, the linkage that mechanically couples the jaws 21, 23 to the actuator 15 may be electrically conductive, and is used to couple RF energy received at the contact region 17 to the electrode 25 at jaw 21 (and/or electrode at jaw 23). For example, the linkage may be slidably coupled to the contact region 17.

Figure 2:
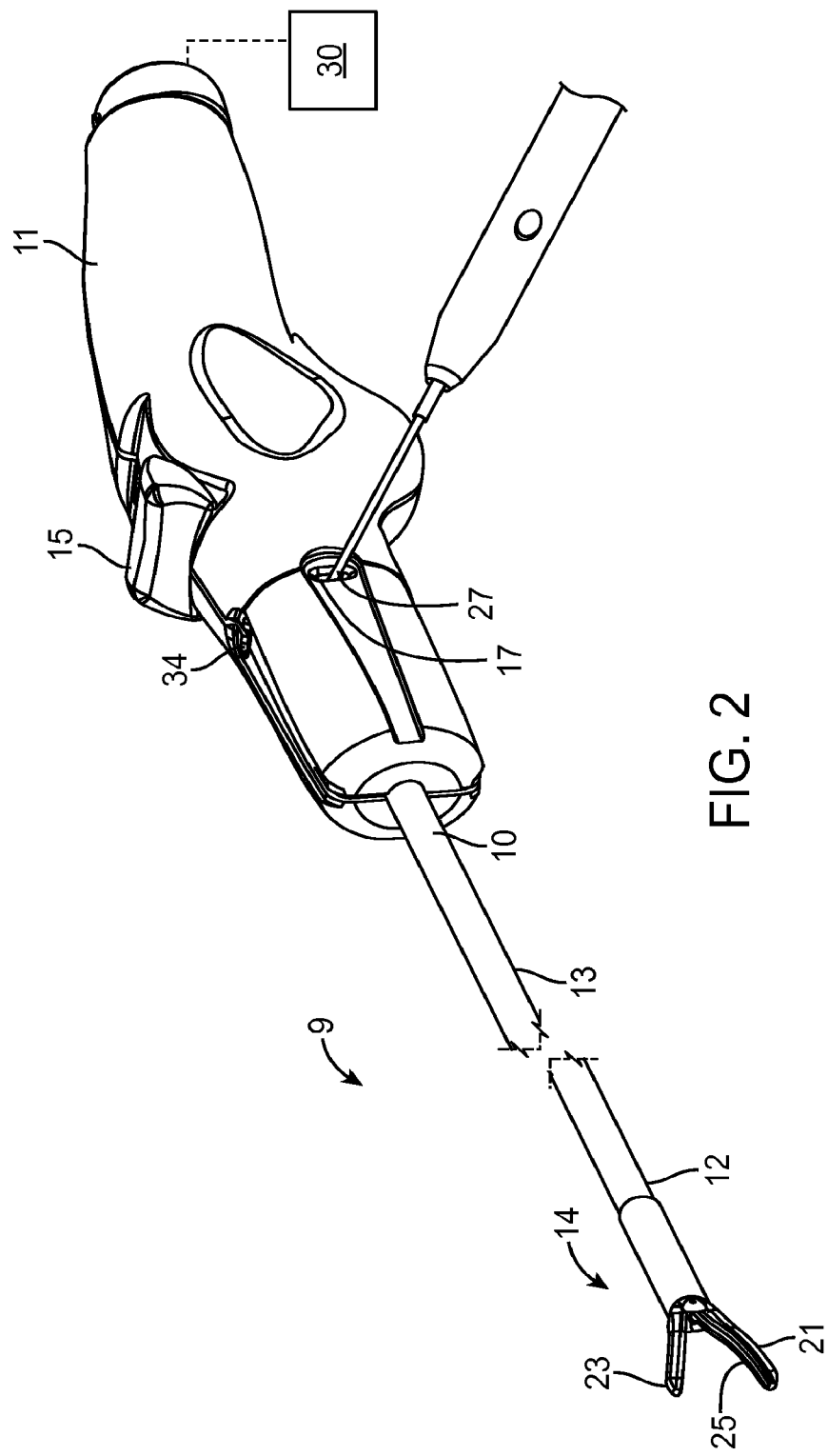
FIGS. 2 and 3 are partial perspective views of another surgical instrument that includes a port for receiving RF energy supplied by another instrument in accordance with some embodiments.
Figure 3:
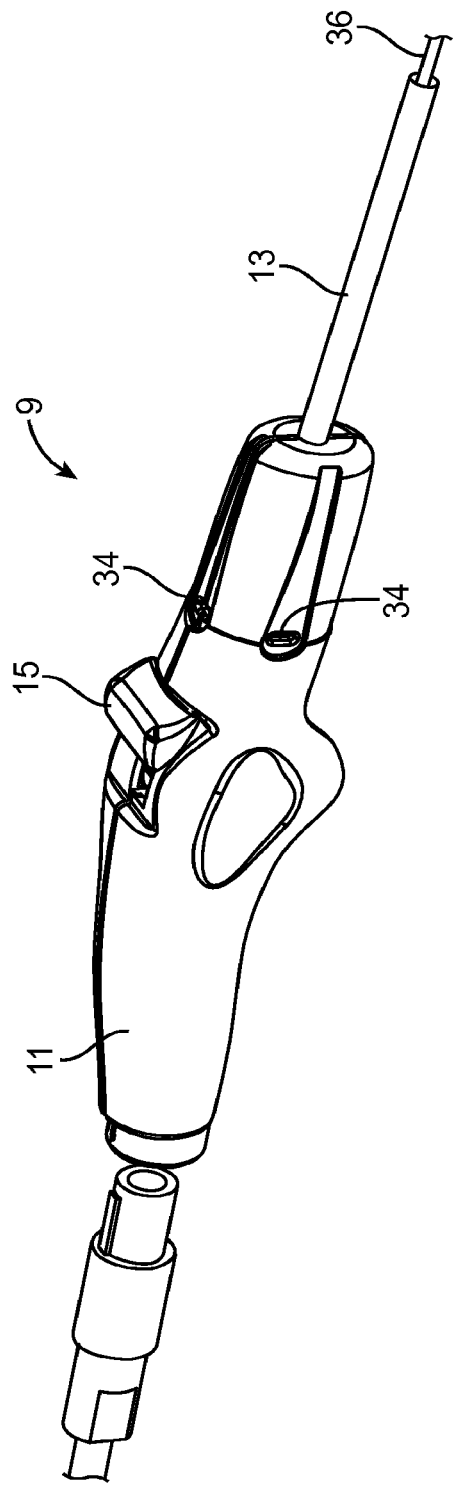

As shown in FIGS. 1, 2, and 3, the connection ports 34 are disposed about the periphery of the handle 11 near its distal end 16. Each such connection port 34 is configured to selectively receive the tip of an electrosurgical RF probe 27, thereby allowing the respective contact terminal 17 to electrically connect such a probe 27 through the electrical line housed in the body 13 (or through the mechanical linkage, e.g., an actuating rod 36, within the body 13 if the linkage is electrically conductive) to the electrically conductive material 25 at the distal end. By providing a plurality of ports 34 circumferentially about the distal portion of the handle 11, the surgical instrument 9 allows the RF probe 27 to make contact with a terminal 17 no matter how the elongated body 13 is oriented about is longitudinal axis. In the illustrated embodiments, the actuating rod 36 is mechanically linked to the actuator 15 in conventional manner to slidably translate within the elongated body 13 in response to fore and aft movements of the actuator 15. Translational movement of the actuating rod 36 is linked to the jaws 21, 23 in conventional manner to open and close the jaws in response to movement of the actuator 15. As illustrated in the embodiments, providing port(s) 34 and contact terminal(s) 17 in the port(s) 34 in this exemplary configuration prevents unintentional contact of the contact terminal(s) by the user during use. In other embodiments, instead of providing port(s) 34 at the handle 11, the port(s) 34 may be provided at the elongated body 13.

In operation, as illustrated in FIG. 2, the contact terminal 17 in the handle 11 of the surgical instrument 9 is contacted by the electrode 27 of an electrosurgical RF probe (e.g., a conventional BOVIE pencil) which is electrically coupled to a high frequency energy source (e.g., electrosurgical RF generator), through any one of the ports 34. The manual contact of the contact terminal 17 by the electrode 27 may be effected from any convenient angle of the electrosurgical RF probe relative to the longitudinal axis of the elongated body 13, and at any angular orientation of the elongated body 13 (about its longitudinal axis). As illustrated in the figure, the contact terminal 17 in each of the ports 34 allows delivering of high frequency energy from the electrosurgical RF generator to the electrosurgical RF probe, and to the electrode 25 of the surgical device 14. A return monopolar RF electrode that may be in a form of a pad (not shown) is coupled to the skin of the patient, and is electrically connected to a terminal of the RF generator. Thus, RF energy is delivered at the electrode 25, and is returned to the RF generator via the return monopolar RF electrode.

In other embodiments, instead of having a contact terminal that is for contact with the electrosurgical RF probe, the surgical instrument 9 may include an additional button (not shown) located at the handle 11. The additional button may be thumb-actuated, and is configured to electrically couple the electrically conductive material 25 at the surgical device 14 to a RF source, wherein the RF source is configured to provide high frequency energy to the surgical instrument 9 (i.e., to the electrically conductive material 25 at the surgical device 14) via a cable. In some embodiments, the surgical instrument 9 provides two modes of operation. In a first mode of operation, when the additional button is actuated, the electrically conductive material 25 is electrically coupled to the RF source, which supplies RF energy to the electrically conductive material for RF cauterization. Also, in the first mode of operation, when the additional button is actuated, the electrically conductive material 25 is electrically decoupled from the DC source 30 so that current cannot be provided to the electrically conductive material 25 from the DC source 30 for heating the electrically conductive material 25 (e.g., even if the actuator 15 is actuated). In a second mode of operation, when the additional button is de-actuated, the electrically conductive material 25 is electrically coupled to the DC source 30, so that the DC source 30 can supply a current to the electrically conductive material 25 for heating the electrically conductive material 25. In other embodiments, when the additional button is de-actuated, the electrically conductive material 25 is allowed to be electrically coupled to the DC source 30 by activation of the actuator 15. In such cases, the electrically conductive material 25 is decoupled from the RF source when the additional button is deactuated, and is electrically connected to the DC source 30 upon actuation of the actuator 15.

It should be noted that the term "first mode" does not need to be associated with supplying RF energy, and that the term "second mode" does not need to be associated with supplying heat energy. As used in this specification, the terms "first mode" and "second mode" refer to different modes. Thus, in other embodiments, the first mode of operation may be achieved by supplying heat energy, and the second mode of operation may be achieved by supplying RF energy. Also, it should be noted that the operation of the additional button may be reversed in other embodiments. In particular, in other embodiments, actuating the additional button would enable delivery of heat energy (and disallow delivery of RF energy), and de-actuating the additional button would enable delivery of RF energy (and disallow delivery of heat energy).

In the illustrated embodiments, operation of the actuator 15 allows selective delivery of heat energy or RF energy in different modes of operation. In some embodiments, activating the actuator 15 will result in closing of the jaw assembly. The activating of the actuator 15 will also configure an internal switch, which allows a current to be delivered to the conductive material 25 for providing heat, and prevents energy from the RF source from being delivered to the conductive material 25. When the actuator 15 is de-activated, the internal switch is configured in a different way, which allows RF energy to be delivered to the conductive material 25, and prevents energy from the DC source 30 from being delivered to the conductive material 25. The internal switch will be described in further detail below with reference to FIGS. 7-10.

Figure 4A:
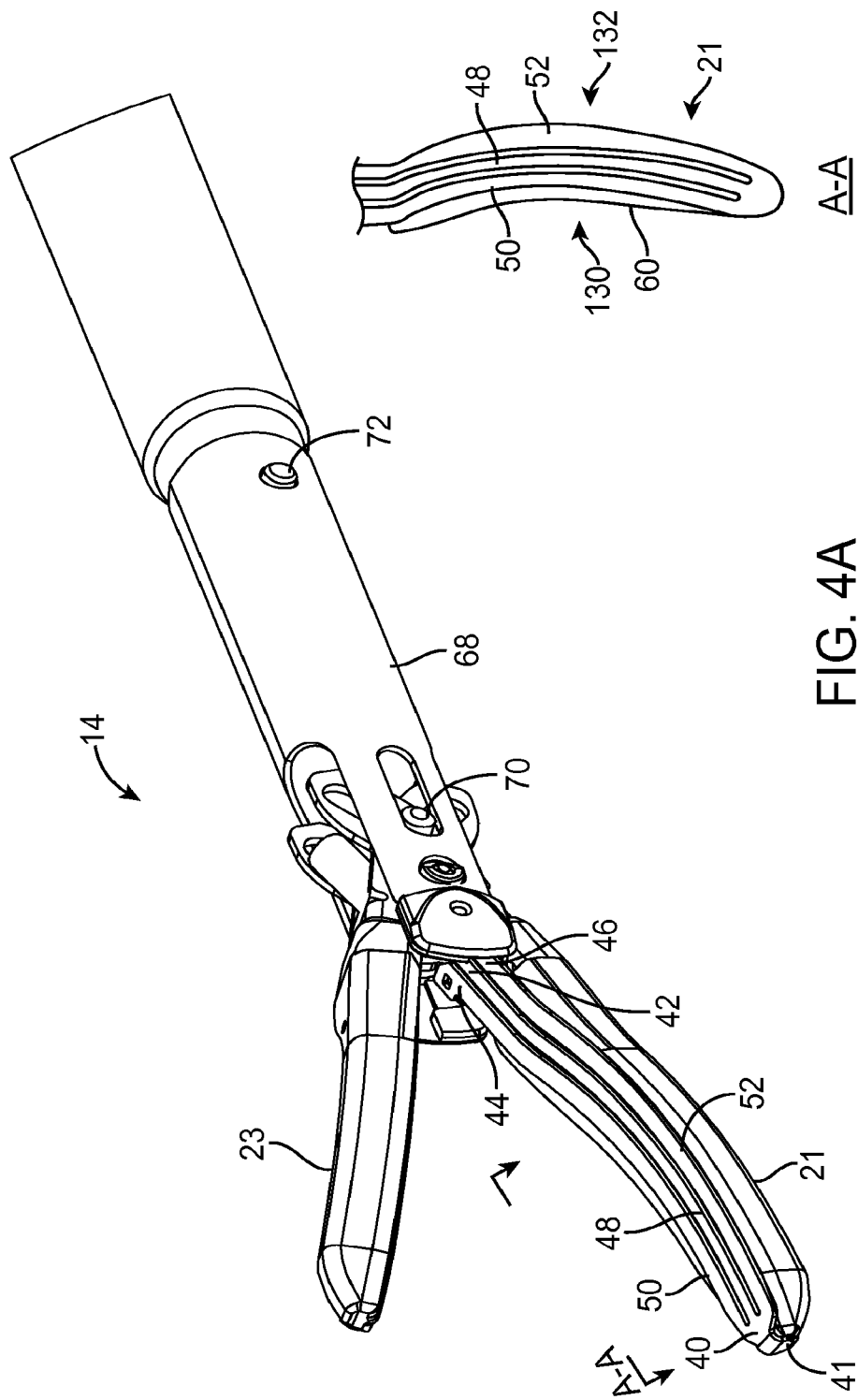
FIG. 4A is a partial perspective view of a pair of jaws in accordance with some embodiments.

FIG. 4A illustrates the pair of jaws 21, 23 in accordance with some embodiments. As shown in the figure, the electrically conductive material 25 forms a heating element (electrode) 40 that is disposed on a surface of the jaw 21. The heating element 40 includes two outer portions 50, 52, and an inner (middle) portion 48. The outer portions 50, 52 have respective outer terminals 44, 46 at their ends, and the middle portion 48 has an inner terminal 42 at its end. Thus, the portions 48, 50, 52 form an electrical heater circuit between the inner terminal 42 and outer terminals 44, 46. In the illustrated embodiments, the outer portions 50, 52 and the inner portion 48 function as an electrode that is configured to deliver heat in one mode of operation, and deliver RF energy in another mode of operation. In particular, in one mode of operation, the terminal 42 of the electrode 40 is electrically coupled to a first terminal of the DC source 30, and outer terminals 44, 46 of the electrode 40 are electrically coupled to a second terminal of the DC source 30, thereby allowing the electrode 40 to receive and conduct DC energy (e.g., for cutting and/or welding tissue). In another mode of operation, the electrode 40 is electrically coupled to a RF source for receiving RF energy (e.g., to provide RF cauterization for bleeding control). The heating element 40 may be formed using a single, flat sheet of electrically conductive material (e.g., Ni-chrome alloy, such as stainless steel at an outer layer, and Ni-chrome at an inner layer). This has reliability, manufacturing and cost advantages. It also reduces the likelihood of tissue build up and entrapment during use by minimizing crevices into which tissue can migrate. Optionally, a distal end 41 of the heater element 40 may be disposed beyond the distal end of the jaw 21 (at the distal tip) to serve as an exposed RF monopolar electrode. This allows cauterization of tissue by RF energy to be performed using the distal tip of the jaw 21.

Figure 4B:
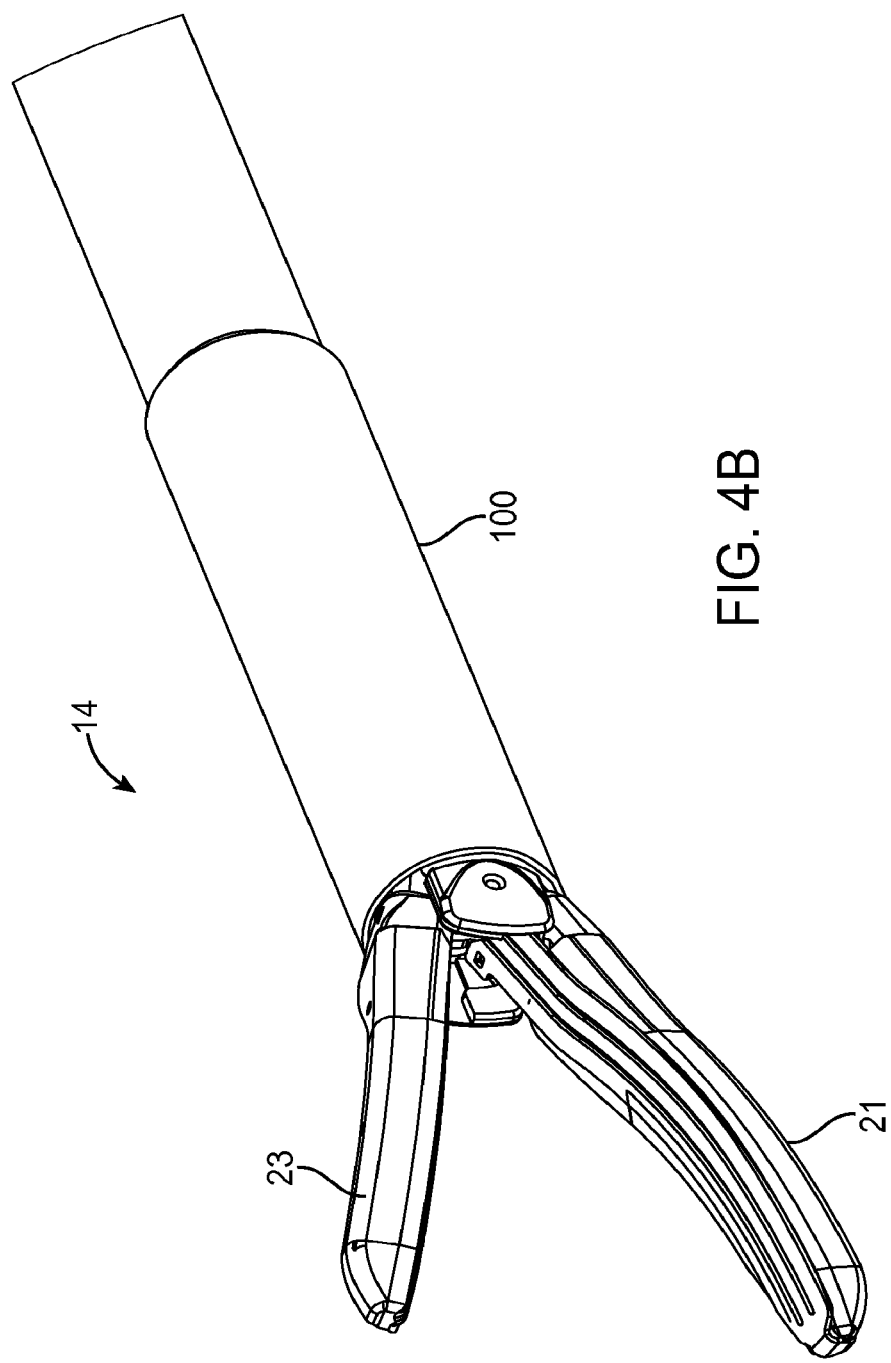
FIG. 4B shows the device of FIG. 4A, showing that the device has an insulative element.

As shown in FIG. 4A, the jaw-operating mechanism and linkage of such mechanism to the actuating rod 36 (not shown) may be supported in a metal housing 68 that includes metal sliding pin 70 and attachment pin 72, all covered with an insulating layer 100 (FIG. 4B) of flexible material such as silicone rubber, or the like, to shield/protect adjacent tissue from moving parts and from electrical energy within the instrument. Also, such an insulating cover retains the sliding and attachment pins 70, 72 in place to obviate the need for more expensive fasteners and mechanisms.

During use, in the first mode of operation, current from the DC source 30 is conducted through the inner terminal 42, and flows in the inner (middle) portion 48 of the heating element 40 and in parallel through the dual outer portions 50, 52 of the heating element 40 to the outer terminals 44, 46. Thus, for heater portions 48, 50, 52 of equal thicknesses and equal widths, current density in the inner (middle) portion 48 is twice as high as the current density in each of the outer portions 50, 52 in response to electrical heater signal (e.g., voltage) applied between inner terminal 42 and the outer terminals 44, 46. Of course, current densities in the inner and outer portions 48, 50, 52 may be altered (for example, by altering the relative widths of the heater portions, by altering resistances through selection of different materials, by altering both the widths and resistances, etc.) to alter the operating temperatures thereof in response to applied electrical heater signals. In operation, the outer portions 50, 52 may operate at a temperature sufficient to weld a tissue structure (e.g., a blood vessel) grasped between the jaws 21, 23, and the inner portion 48 may operate at a higher temperature sufficient to sever the grasped tissue structure intermediate of the welded segments. In the second mode of operation, the heater element 40 does not receive current from the DC source 30. Instead, the heater element 40 operates as a RF electrode (e.g., a monopolar electrode) and delivers RF energy that is provided from the RF generator, and that is transmitted to the heater element 40 via the contact terminal 17. The application of the RF energy may be used to control bleeding in surrounding tissues at the surgical site, e.g., tissue that is next to the vessel being harvested, or tissue next to a side branch vessel, etc.

Figure 5A:
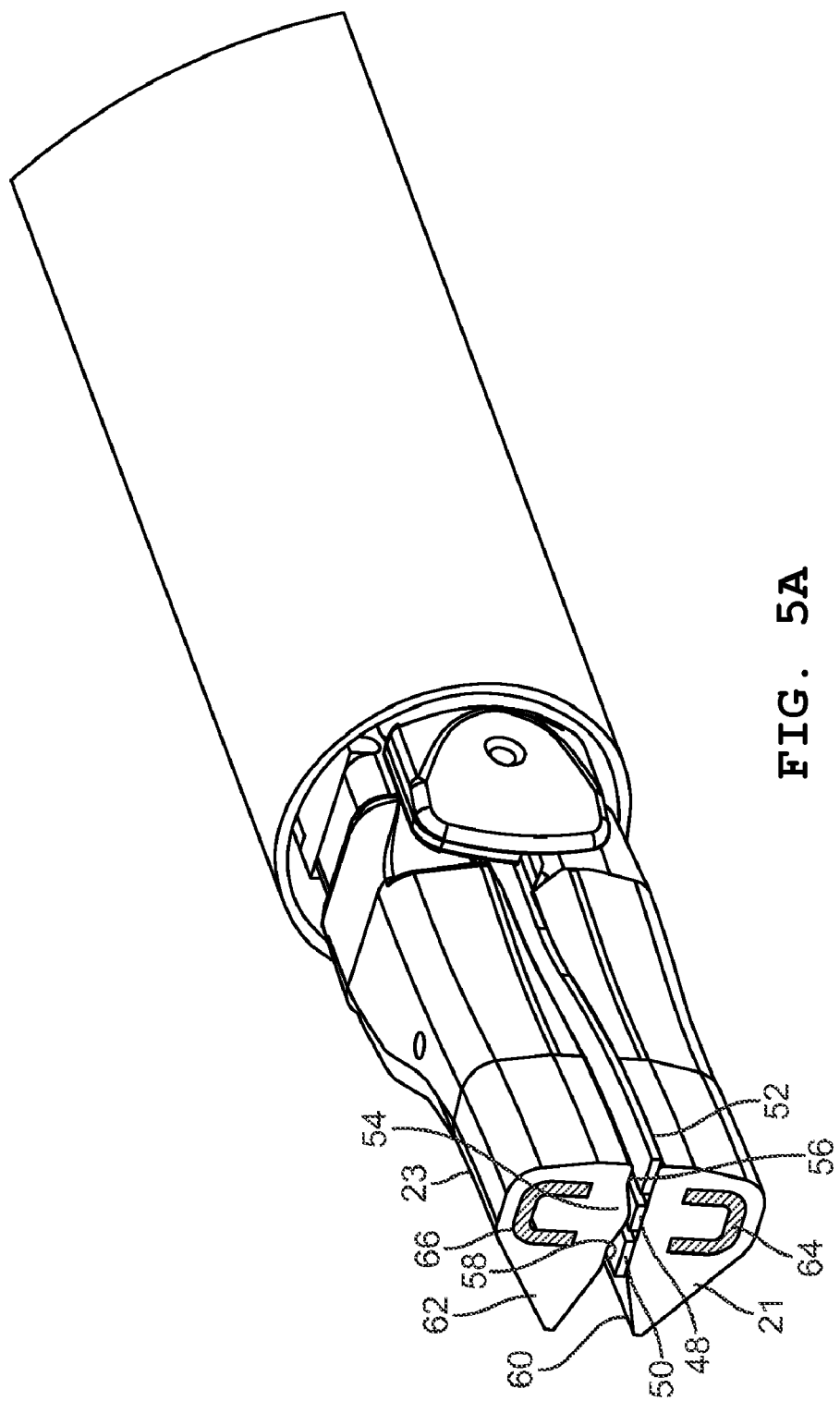
FIG. 5A is a cross sectional view of the pair of jaws of FIG. 4A in accordance with some embodiments.

Referring now to FIG. 5A, there is shown a partial cross sectional view of the jaws 21, 23 that illustrates the placement of inner and outer portions 48, 50, 52. The jaw 21 includes a structural support 64, and the jaw 23 includes a structural support 66. In some embodiments, the structural supports 64, 66 may be made from electrically conductive material that allows the supports 64, 66 to function as electrical lines (e.g., for transmitting current, RF signal, etc.). The structural supports 64, 66 are covered by respective layers of electrically insulating material, such as rubber, polymers, silicone, polycarbonate, ceramic or other suitable insulating material. The layers may be molded separately and bonded onto the respective structural supports 64, 66. Alternatively, the layers may be over-molded onto the structural supports 64, 66. For example, each of the structural supports 64, 66 may have one or more openings for allowing the material of the respective layers to flow therethrough during the over-molding process. As shown in the figure, the jaw 23 includes a surface elevation (protrusion) 54 substantially in alignment with the inner (middle) portion 48 in order to increase the compression force applied to a tissue structure grasped by the jaws 21, 23 and in contact with the middle portion 48. This promotes more efficient tissue severance, while adjacent regions 56, 58 of lower surface elevations on jaw 23 in alignment with the outer portions 50, 52 of the heating element introduce less compression force suitable for welding grasped tissue.

Figure 5B:
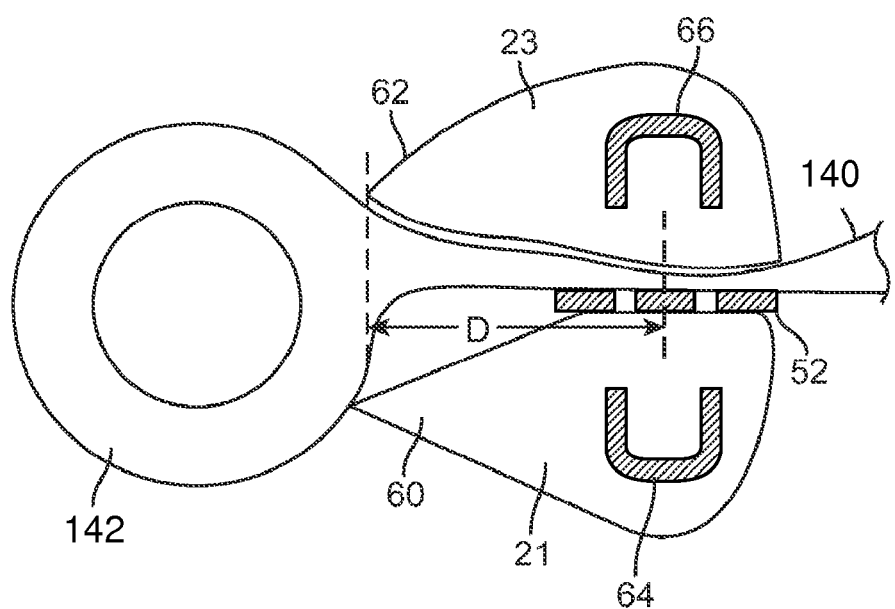
FIG. 5B is a cross sectional view of the pair of jaws of FIG. 4A, showing the jaws being used to cut a side branch vessel.

In the illustrated embodiments, the cross sections of the respective jaws 21, 23 are not symmetrical. Instead, jaw 21 has a protrusion 60, and jaw 23 has a protrusion 62. Each of the protrusions 60, 62 has a length so that when the protrusions 60, 62 abut against a main vessel 142, the cutting point of the side branch vessel 140 is at a prescribed (predetermined) distance D that is spaced away from the main vessel 142 (FIG. 5B). In the illustrated embodiments, the distance D is at least 1 mm, and more preferably, at least 1.5 mm. In other embodiments, the distance D may have other values, such as that which is sufficient to prevent or minimize thermal spread from electrode 40 to the main vessel 142 being harvested. As illustrated in the embodiments, the protrusions 60, 62 help prevent or minimize thermal spread to the main vessel 142 from the cutting and sealing of the side branch vessel 140, thereby preserving the integrity of the main vessel 142 that is being harvested. Also, the protrusions 60, 62 obviate the need for an operator to guess whether the cutting of the side branch vessel 140 is sufficiently far (e.g., beyond a minimum prescribed spacing) from the main vessel 142. Instead, the operator merely abuts the protrusions 60, 62 of the jaw assembly against the main vessel 142, and the protrusions 60, 62 will automatically place the jaw assembly relative to the side branch vessel 140 so that the side branch vessel 140 is cut at a minimum prescribed distance D from the main vessel 142. In some cases, if the surgical instrument 9 is used to cut other types of tissue, such as nerves, organs, tendons, etc., the protrusions 60, 62 also provide the same benefits of preserving the integrity of tissue adjacent to the cut, and obviating the need for a user to guess the appropriate margin. As shown in the figure, the protrusions 60, 62 diverge away from part of the side branch vessel 140. Such a configuration allows part of the side branch vessel 140 that is immediately next to the main vessel 142 not to be clamped by the jaws. As a result, the severed end of the side branch vessel 140 will fall away once it is cut. In other embodiments, the surgical instrument 9 does not need to include both protrusions 60, 62. Instead, the surgical instrument 9 may include either protrusion 60 or protrusion 62. Such a configuration allows the device at the distal end of the instrument 9 to have a smaller profile, thereby allowing a user to effectively maneuver the distal device in tight tissue conditions. As shown in the figure, the outer portion 52 may protrude laterally along an outer edge of the closed jaws 21, 23 to serve as an RF electrode for RF signal applied thereto, in a manner described herein, while the outer portion 50 is shrouded or recessed within the lateral protrusions 60, 62 on the jaws 21, 23 to limit emission of applied RF signal from along mainly (or only) the exposed edge of the outer portion 52.

As shown in FIG. 4A, the jaw assembly has a concave side 130 and a convex side 132. In one method of use, while the jaw assembly is used to cut a side branch vessel 140, the jaw assembly is oriented so that its concave side faces towards the main vessel 142. An endoscope or viewing device may be placed next to the jaw assembly with the endoscope or viewing device viewing the concave side of the jaw assembly. This allows the user to better visualize the tip of the jaw assembly. Such configuration also provides a safety benefit by allowing the user to know where the tips are during the vessel cutting procedure. Also as shown in FIG. 6, the exposed outer portion 52 is on the convex side of the jaw assembly while the protrusions 60, 62 are on the concave side of the jaw assembly. The concavity provides extra spacing to further protect the main vessel 142 when the side branch vessel 140 is grasped. Furthermore, the exposed outer portion 52 on the convex side creates a protrusion that makes it easier to contact the wall of the tunnel with the exposed outer portion 52 to address bleeding. In other embodiments, the protrusions 60, 62 may be on the convex side of the jaw assembly while the exposed outer portion 52 is on the concave side. In such cases, during use, the convex side of the jaw assembly would be oriented towards the main vessel 142, thereby ensuring that the tips of the jaw assembly are separated from the main vessel 142 to enhance protection (e.g., preventing the tip of the jaw assembly from touching or injuring the main vessel 142).

Figure 7B:
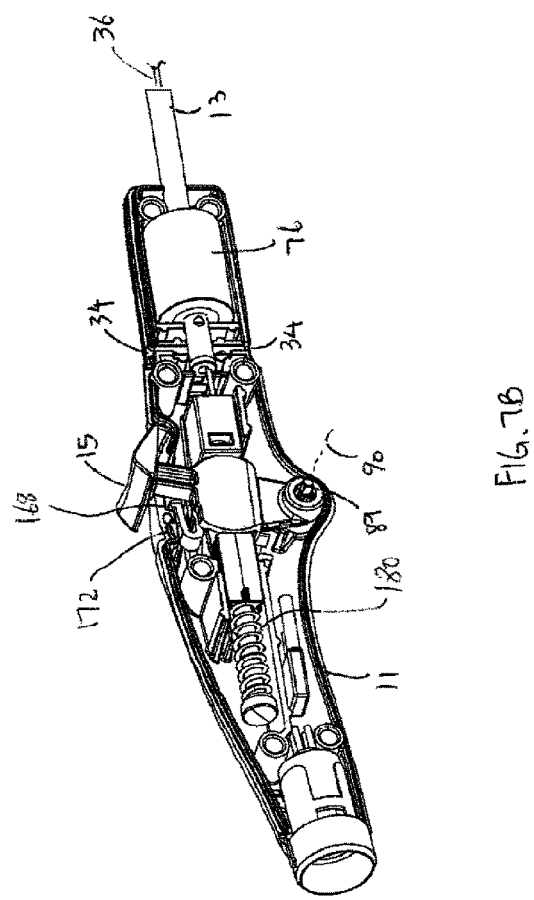
Figure 8:
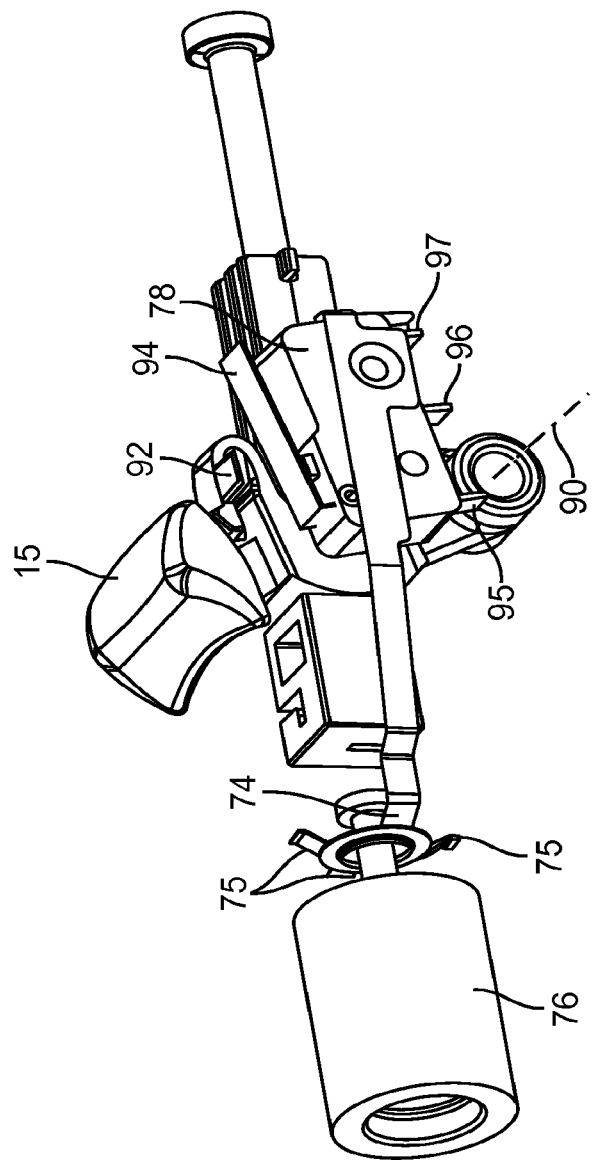
FIG. 8 illustrates some components of the handle of FIG. 1 in accordance with some embodiments.
Figure 10:
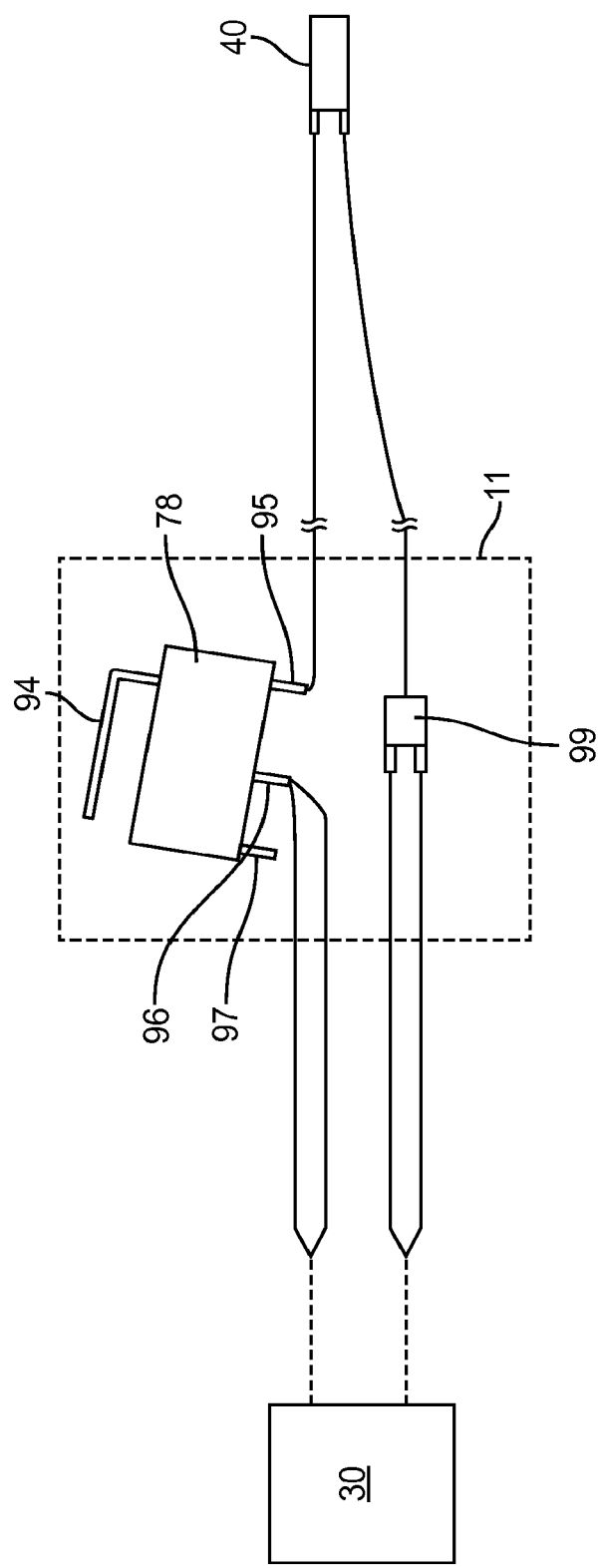
FIG. 10 illustrates how the electrical switch in the handle of FIG. 1 is connected to a power source and to an electrode in accordance with some embodiments.

Referring now to the partial cutaway view of FIGS. 7A and 7B, which shows some of the interior components of the handle 11. As shown in FIG. 7A, an electrical switch 78 is mounted in the handle 11 to be operated in conjunction with the actuator 15 (not shown in FIG. 7A for clarity) for controlling electrical power supplied to the inner and outer portions 48, 50, 52. As shown in FIG. 7B, the actuator 15 is rotatably mounted to the handle 11 via a shaft 89 so that the actuator 15 is pivotable about axis 90. When mounted to the handle 11, the actuator 15 is located next to the electrical switch 78 in a side-by-side configuration. As shown in FIG. 8, the actuator 15 has a tab portion 92 for engagement with a lever 94 of the switch 78. The switch 78 has a first contact (common contact) 95, a second contact (normally-open contact) 96, and a third contact (normally-closed contact) 97. The first contact 95 is electrically connected to a terminal of the heating element (electrode) 40 (e.g., via a wire), and the second contact 96 is electrically connected to a first terminal of the DC source 30 (FIG. 10). Another terminal of the heating element (electrode) 40 is electrically connected to a second terminal of the DC source 30 (FIG. 10). As shown in FIG. 10, at least two wires can be used to connect the first terminal of the DC source 30 to the second contact 96 at the switch 78, and at least two wires can be used to connect the second terminal of the source 30 to a fuse 99 that is coupled to the electrode 40. The fuse 99 is a safety device for preventing overheating of the surgical instrument 9. In some embodiments, if the heating circuit's temperature is above a certain prescribed threshold, the fuse 99 will prevent a current from being delivered to the electrode 40. Having two wires for each terminal of the DC source 30 is provides redundancy, so that switch 78 functions even if one of the wires for any of the terminals at the DC source 30 is broken. In other embodiments, the surgical instrument 9 may include only one wire connecting terminal 96 to the source 30, and only one wire connecting the fuse 99 to the source 30. As shown in FIG. 8, a contact device 74 is electrically connected to the third contact 97 of the electric switch 78. In the illustrated embodiments, the contact device 74 is used to implement the contact terminal(s) 17. Electrical switches that may be used with the handle 11 are commercially available from E-Switch, at Brooklyn Park, Minnesota. The handle assembly 11 is completed with a complementary half section (not shown) that snaps together with, or is otherwise attached to the illustrated half section. The handle 11 is formed of plastic material that also provides electrical insulation from RF emissions while the surgical instrument 9 is connected with the RF generator in the manner as previously describe herein. In some cases, the material for construction of the handle 11 is selected so that it provides adequate strength for the handle 11 to withstand forces of the mechanisms and forces of the user interacting with the instrument during a procedure.

Figure 9A:
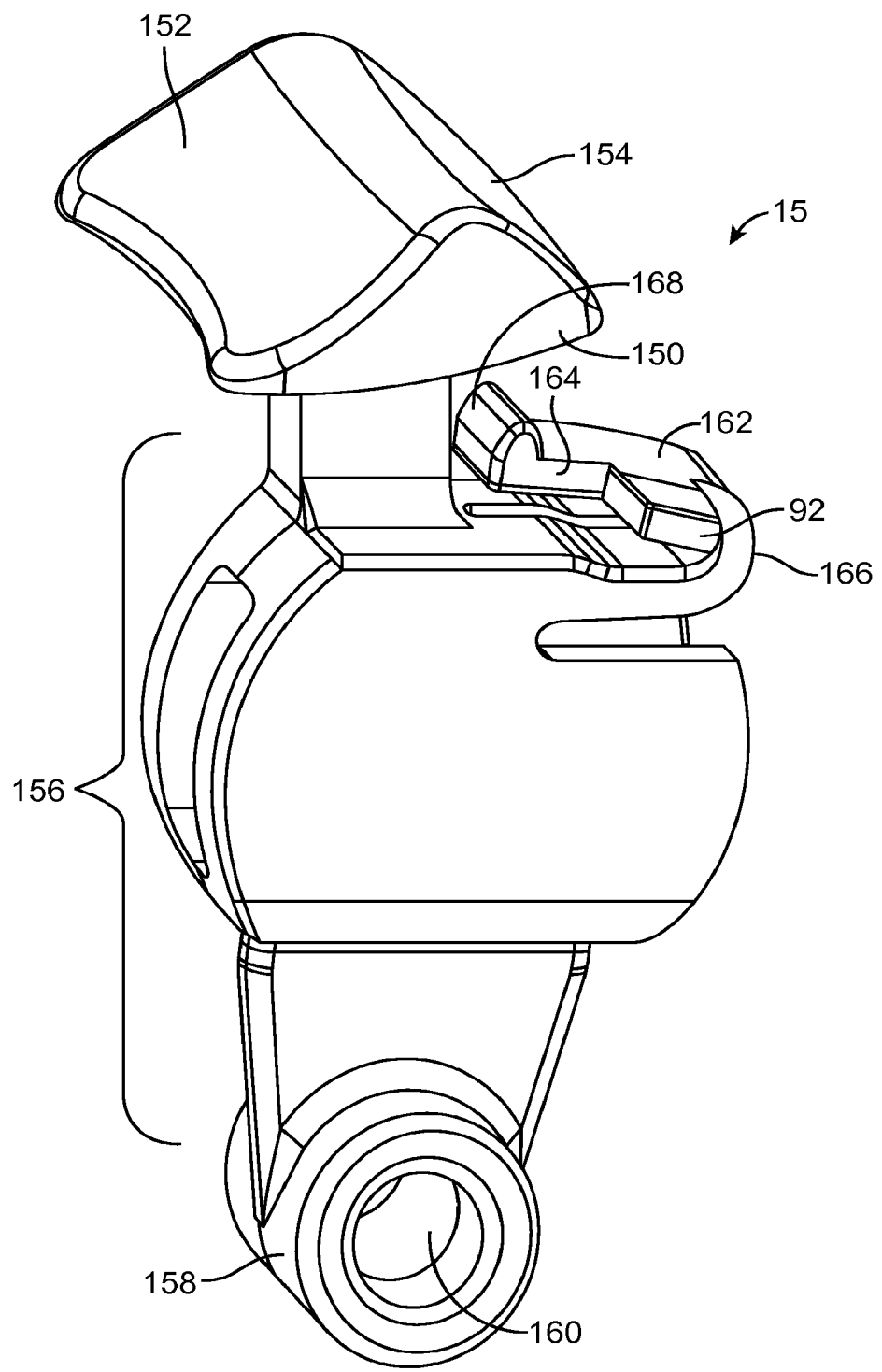

As shown in FIG. 9A, the actuator 15 has a button 150 with a distal portion 152 and a proximal portion 154. The actuator 15 also has a body 156 extending from the button 150 to an end 158 with a slot 160 for accommodating a shaft. The actuator 15 further includes a spring lever 162 having a free end 164, and is connected to the body 156 via a bent end 166. The free end 164 of the lever 162 has a protrusion 168 for engaging with a corresponding portion at the housing of the handle 11. The spring lever 162 also has a tab portion 92 for engagement with the lever 94 of the electrical switch 78 during use. As shown in FIG. 8, when the actuator 15 is pulled proximally, the tab 92 will be brought into engagement with the lever 94 of the switch 78, and the switch lever 94 will be deflected by the tab portion 92. The deflection of the switch lever 94 will activate the switch 78, causing energy to be delivered from the source 30 to the electrode 25 via the switch 78. At the same time that the tab portion 92 deflects the switch lever 94, the protrusion 168 of the actuator 15 engages with the detent portion 172 at the housing of the handle 11. The detent portion 172 at the handle 11 deflects the spring lever 162 of the actuator 15 (due to the ramp surface at the protrusion 168) as the actuator 15 is pulled proximally, thereby providing a tactile feedback to the user.

In other embodiments, the protrusion 168 is configured to engage the detent portion 172 first before the tab portion 92 fully activates the switch 78. In such cases, the user will feel a resistance when the protrusion 168 engages with the detent portion 172 at the handle 11. The user may then continue to pull the actuator 15 proximally with an increase of pulling force. The increased pulling force will cause the detent portion 172 to deflect the spring lever 162 downward, until the protrusion 168 traverses the detent portion 172; at this point, the user will feel a decrease in pulling force. At the same time that the spring lever 162 is deflected, the actuator 15 is allowed to be pulled proximally further, thereby causing the tab portion 92 to deflect the lever 94 of the switch 78.

Figure 9G:
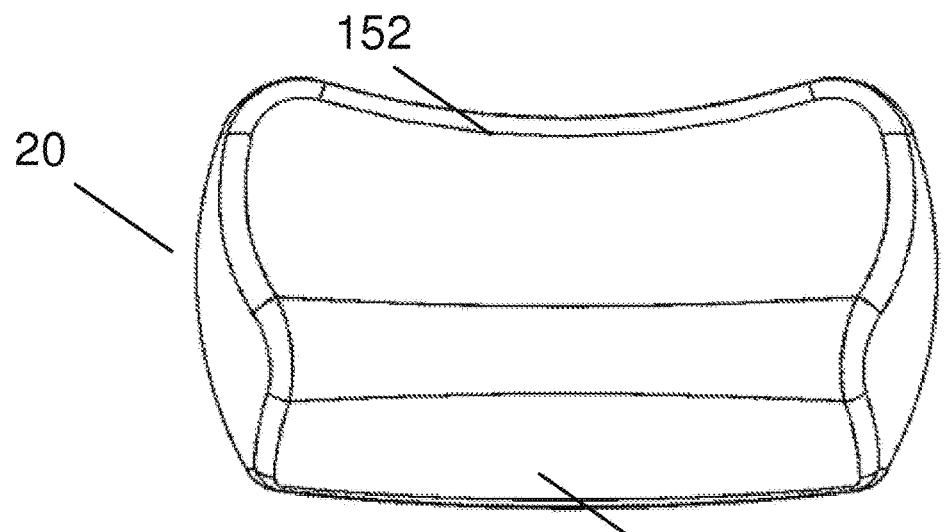
Figure 9F:
Figure 9E:
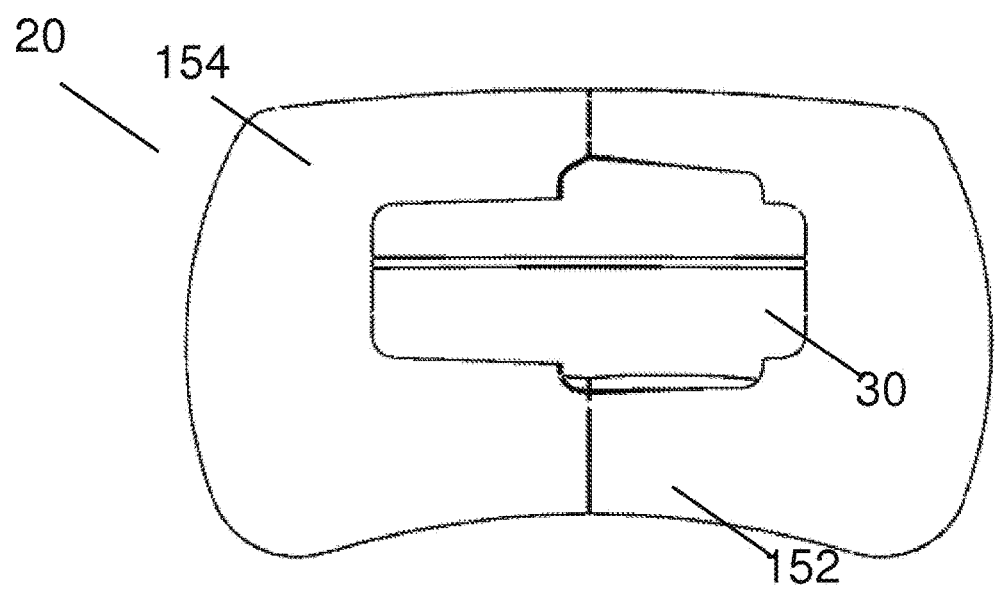

In the illustrated embodiments, all of the components of the actuator 15 have a unity construction except for the over-molded piece 20 on button 150. Such configuration obviates the need to mechanically connect the different components together, and reduces manufacturing costs. For example, by constructing the spring lever 162 with the rest of the actuator 15 as one component, the material connecting the spring lever 162 to the body 156 of the actuator 15 will function as a joint and spring, thereby obviating the need to provide a separate connector for connecting the lever 162 to the body 156, and a separate spring element (e.g., a coil) for providing the resiliency for the lever 162. FIGS. 9B-9D illustrate respectively side, distal and perspective views of the actuator 15 without the over-molded piece 20 disposed on button base 38. FIGS. 9E-9G respectively illustrate bottom, distal and top views of the over-molded piece. FIG. 9E illustrates an exemplary cavity 35 created by the over-molding process, inside of which fits button base 38. As an alternative embodiment, all of the components of the actuator 15 including button 150 have a unity construction.

In the illustrated embodiments, the distal portion 152 of the actuator 15 has a concave configuration, and the proximal portion 154 of the actuator 15 has a convex configuration. During use, a user may place his/her finger in the recess of the concave surface at the distal portion 152, and pull the actuator 15 proximally relative to the handle 11. In some embodiments, the pulling of the actuator 15 causes the jaw assembly at the distal end to close and activates the electrode 25 at the distal end of the surgical instrument 9. The user may also place his/her finger at the convex surface at the proximal portion 154, and push the actuator 15 distally relative to the handle 11. In the illustrated embodiments, pushing the actuator 15 distally causes the jaw assembly at the distal end to open and deactivates the electrode 25. In other embodiments, the actuator 15 and the mechanism inside the handle 11 may be configured to produce the opposite effects. For example, in other embodiments, pushing the actuator 15 distally may cause the jaw assembly at the distal end to close and may activate the electrode 25 at the distal end of the surgical instrument 9, and pulling the actuator 15 proximally may cause the jaw assembly to open and may deactivate the electrode 25.

The asymmetric configuration of the button 150 of the actuator 15 provides an intuitive interface for allowing the user to control the actuator 15. For example, if the actuator 15 is configured to close the jaw assembly and activate the electrode 25 when the actuator 15 is pulled proximally relative to the handle 11, then the user will know that he/she is closing the jaw assembly and/or activating the electrode 25 as soon as he/she places the finger in the concave surface at the distal portion 152 of the button 150. The user will also know that he/she is opening the jaw assembly and/or deactivating the electrode 25 as soon as he/she places the finger on the convex surface at the proximal portion 154 of the button 150. This is because the different configurations at the distal and proximal portions 152, 154 provide different tactile information to the user, thereby informing the user of the different modes of operation of the actuator 15.

In the illustrated embodiments, a compression spring 180 (shown in FIG. 7B) may be used to bias the actuator 15 in a distal direction. When pulling back on the actuator 15, the user has to overcome the resistance of both the detent portion 172 and the spring 180. On the other hand, when pushing the actuator 15 distally, the user may receive assistance from the spring 180 because the spring 180 is under compression. As a result, the user may feel different resistances to motion, depending on whether he/she is pulling or pushing the actuator 15. In other embodiments, the button 150 of the actuator 15 may have different types of asymmetric configurations. For example, in other embodiments, the distal portion 152 may have a surface with a first type of texture (e.g., bumps), and the proximal portion 154 may have a surface with a second type of texture (e.g., no bumps) that is different from the first type. In further embodiments, the distal portion 152 may be made from a first material, and the proximal portion 154 may be made from a second material that is different from the first material (e.g., softer, stiffer, more compliant, less compliant, etc.). Such configuration, either along, or in combination with the spring 180 and detent portion 172, provides the actuator 15 with a first resistance to motion when the actuator 15 is operated in one way, and a second resistance to motion that is different from the first resistance when the actuator 15 is operated in another way. In still further embodiments, any of the configurations of the distal and proximal portions 152, 154 may be reversed. For example, in other embodiments, the distal portion 152 may have a convex configuration, and the proximal portion 154 may have a concave configuration. Also, in other embodiments, the protrusion 168 may have an asymmetric configuration to provide different "feels" for the user when the user is pulling and pushing the actuator 15. For example, the ramp may be steeper on one side of the protrusion 168 than the other. Additionally, the actuator 15 may be harder to pull proximally than to push distally. Also, in some embodiments, the distal and proximal portions 152, 154 are both made from compliant materials, but with different degrees of compliance. Such a control would be more comfortable to use than a control that is made from a hard plastic (a non-compliant material).

Returning to FIG. 8, the contact terminals 17 are implemented using a resilient electrical contact device 74 that is disposed within the handle 11. The contact device 74 includes a plurality of resilient contact terminals 17 (each of which may be considered a contact region) that are aligned with respective connection ports 34. Each port 34 allows access by a RF probe, such as a conventional BOVIE pencil, for making contact with the corresponding contact terminal 17 therein. A smoke filter 76 is positioned in the forward end of the handle 11. The filter 76 is for filtering steam/smoke generated during operation of the device (e.g., steam/smoke that results from cutting tissue, welding tissue, and/or bleeding control) so that the steam/smoke will not interfere with the user of the surgical instrument 9, to help improve visualization in the working site, and to reduce the amount of surgical smoke that is introduced into the operating environment. During use, the working tunnel has a pressure differential caused by pressurized gas (e.g., $CO_2$) such that smoke is forced from the tunnel into the device tip, through the interior of the elongated body 13, and into the filter 76 of the handle 11. The actuating rod 36 is mechanically linked in conventional manner to the actuator 15 to slidably translate the actuating rod 36 within the elongated body 13 for remotely operating the jaws 21, 23 between open and closed positions.

During use, when the actuator 15 is pushed forward (by rotating about axis 90) to push actuating rod 36, the translational motion of the actuating rod 36 causes the jaws 21, 23 to open. The opened jaws 21, 23 can then be used to grasp tissue (e.g., side branch vessel). When the jaws 21, 23 are placed around target tissue, the actuator 15 may be pulled backward to pull actuating rod 36. The translational motion of the actuating rod 36 causes the jaws 21, 23 to close, thereby gripping the target tissue. If desired, the actuator 15 may be further pulled backward to cause the tab portion 92 of the actuator 15 to engage the lever 94 of the electrical switch 78. This in turn causes the first contact 95 to be electrically connected to the second contact 96 within the switch 78, thereby supplying DC power from the DC source to the heating element (electrode) 40. Inside the switch 78, when the second contact 96 is electrically connected to the first contact 95, the third contact 97 is electrically decoupled from the first contact 95. Thus, while DC energy is being delivered to the electrode 40 (e.g., for providing heat to cut and/or weld tissue), the contact device 74 will not be able to transmit RF energy (e.g., from an electrosurgical RF probe) to the electrode 40. The delivery of DC energy may be stopped by pushing the actuator 15 forward so that the tab portion 92 is disengaged from the lever 94 of the electrical switch 78. When this occurs, the second contact 96 is electrically disconnected from the first contact 95 inside the switch 78, and the third contact 97 is electrically connected to the first contact 95 inside the switch 78. Such configuration allows RF energy (from the electrosurgical RF probe delivered at the contact device 74 and transmitted to the third contact 97) to be transmitted to the electrode 40 (e.g., to perform RF cauterization for bleeding control). Note that in this mode of operation, DC energy cannot be delivered to the electrode 40 because the first and second contacts of the switch 78 are not electrically connected.

Figure 11:
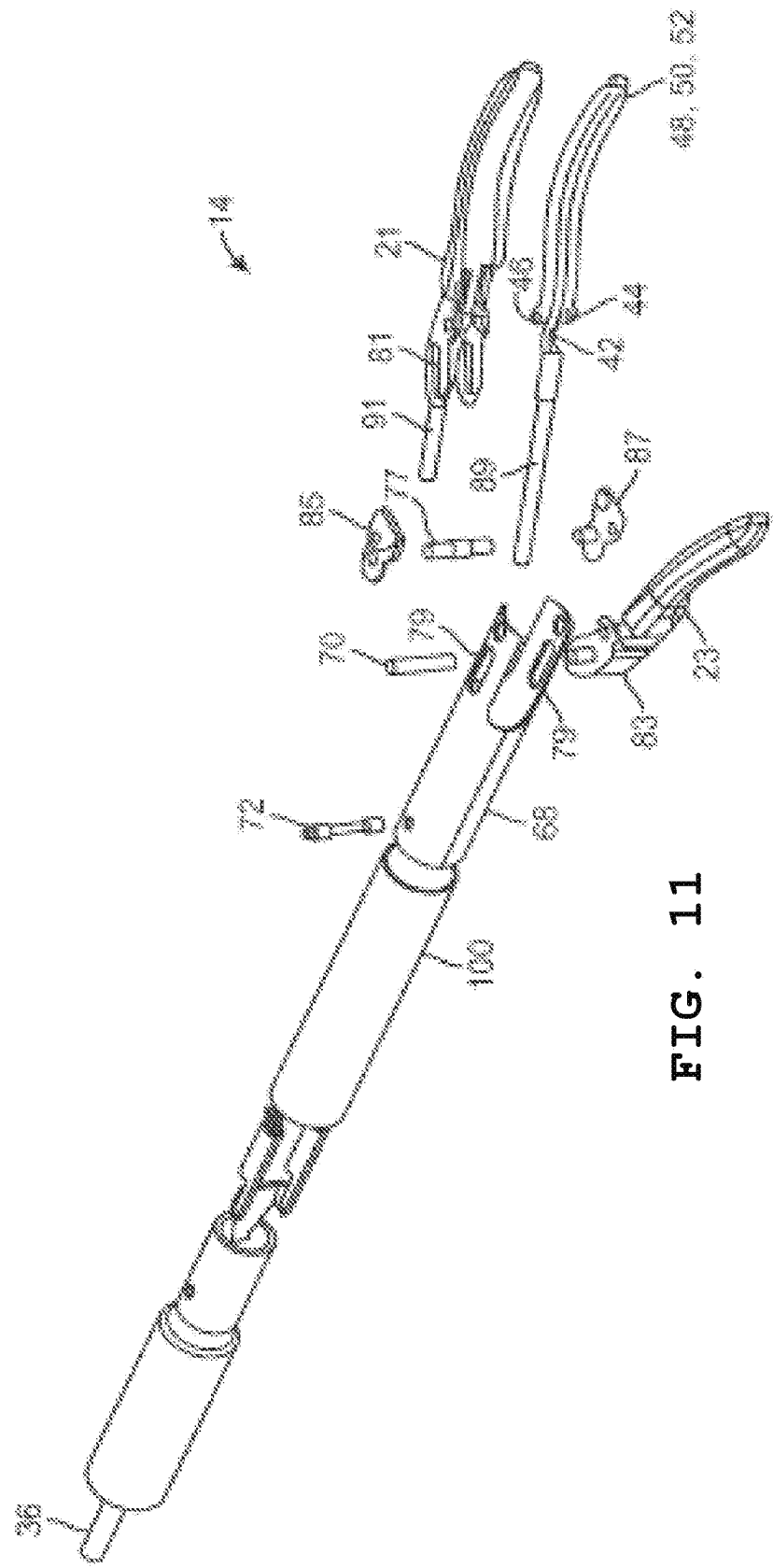
FIG. 11 is a partial exploded view of the components of a surgical instrument in accordance with some embodiments.

Referring now to FIG. 11, there is illustrated an exploded view of the components forming the surgical device 14, and its attachment to the distal end of the elongated body 13. Specifically, the heating element 40, comprising inner and outer portions 48, 50, 52 (conductive material 25), is attached to jaw 21. Both jaws 21, 23 are pivotally attached via insulating material clevises 85 and 87 and pin 77 to the metal housing 68. The jaws 21, 23 pivot on the clevises 85, 87 so that they can be kept electrically isolated from pin 77 which holds inner terminal 42 against the face of jaw 21. Such a configuration prevents the metal structural supports 64, 66 of jaws 21, 23 from contacting the pin 77, avoiding an electrical short circuit. Pin 70 is disposed to slide within the aligned slots 79, and within the mating angled slots 81, 83 in the frame-mounts of the associated jaws to effect scissor-like jaw movement between open and closed positions as the slide pin 70 is moved relative to the pivot pin 77. Actuating rod 36 is linked to the slide pin 70, for example, via a yoke 37 that is attached to the distal end of the actuator rod 36. Axial movement of the actuating rod 36 in one direction will cause the slide pin 70 to move towards the pin 77, thereby opening the jaws 21, 23. Axial movement of the actuating rod 36 in the opposite direction will cause the slide pin 70 to move away from the pin 77, thereby closing the jaws 21, 23. An electrical conductor 89 connects to the inner terminal 42 of the heating element 40, and the outer terminals 44, 46 are electrically connected in common to electrical conductor 91. In some embodiments, either electrical conductor 89 or 91 may be housed within the wall or the bore of the elongated body 13. In other embodiments, if the actuating rod 36 is electrically conductive, either electrical conductor 89 or 91 may be coupled to the actuating rod 36. In such cases, the actuating rod 36 will be electrically coupled to one terminal of the DC source 30, or to the contact 95 of the switch 78, during use. During use, the electrical conductors 89, 91 may be electrically coupled to terminals of the DC source 30, which provides a current to thereby heat up the inner and outer portions 48, 50, 52 of the heating element 40. The center inner portion 48 is configured to cut a vessel (e.g., a side branch vessel) while the outer portions 50, 52 are configured to weld (seal) the vessel. In some embodiments, parts of the surgical device 14 may be insulated via an outer insulating layer for restricting RF emissions (when the bleeding control function is used) and for isolating certain components from biologic tissue and fluids. In the illustrated embodiments, the surgical instrument 9 includes an insulative cover 100.

During use of the surgical instrument 9, the elongated body 13 is advanced along a vessel to be harvested. In some cases, the instrument 9 may be placed into an instrument channel of a cannula which includes a viewing device, such as an endoscope, for allowing an operator to see the distal end of the surgical instrument 9 inside the patient. When a side branch vessel (or other target tissue) is encountered, the jaws 21, 23 may be used to grasp and compress the side-branch vessel in response to manipulation of the actuator 15. Power is then supplied using the DC source 30 to the inner and outer portions 48, 50, 52 of the heating element 40 (which function as resistive elements that heat up in response to the delivered direct current) to effect tissue welds at tissues that are in contact with outer portions 50, 52, and to effect tissue cutting at tissue that is in contact with inner portion 48.

During the vessel harvesting procedure, if the operator notices that there is bleeding in the surrounding tissues (e.g., from the walls of the surgical cavity), the operator may position the electrosurgical RF probe 27 so that it is in contact with the contact terminal 17 through one of the ports 34 at the handle 11. This results in RF energy being supplied (or allowed to be supplied) from the attached electrosurgical RF generator. In some cases, a foot-actuated switch may be provided that allows the operator to direct RF energy from the RF generator to the RF probe 27. The supplied RF energy from the RF generator is conducted to the electrically conductive material 25 at the distal surgical device 14, and the energy is returned via a return electrode pad that is coupled to the skin of the patient. The electrically conductive material 25 serves as a monopole RF electrode to electrocauterize any tissue (e.g., vessel tissue or surrounding tissue) that is grasped between the jaws 21, 23. Alternatively, the lateral edge of the outer portion 52 that protrudes from a side of the jaw 21 may be used to cauterize bleeding area. In such cases, the jaws 21, 23 may or may not be closed, and may or may not be grasping any tissue. For example, in some embodiments, the operator may not be using the jaws 21, 23 to grasp or cut tissue. However, if the operator notices that there is bleeding at or near the surgical site, the operator may use the outer portion 52 protruding from a side of the jaw 21 (e.g., such as that shown in FIG. 6) to cauterize the bleeding area. In particular, the exposed portion of outer portion 52 serves as an RF monopole electrode for electrocauterizing the tissue.

In some embodiments, the exposed portion of the outer portion 52 may also be used as a DC electrode for controlling bleeding. For example, the side or the tip of the outer portion 52 that extends beyond the profile of the jaw assembly may be used to perform thermal spot cauterization by direct thermal conduction. In such cases, the outer portion 52 may be heated up, and its exposed edge (or tip) may be used to touch tissue that is desired to be cauterized.

Figure 12:
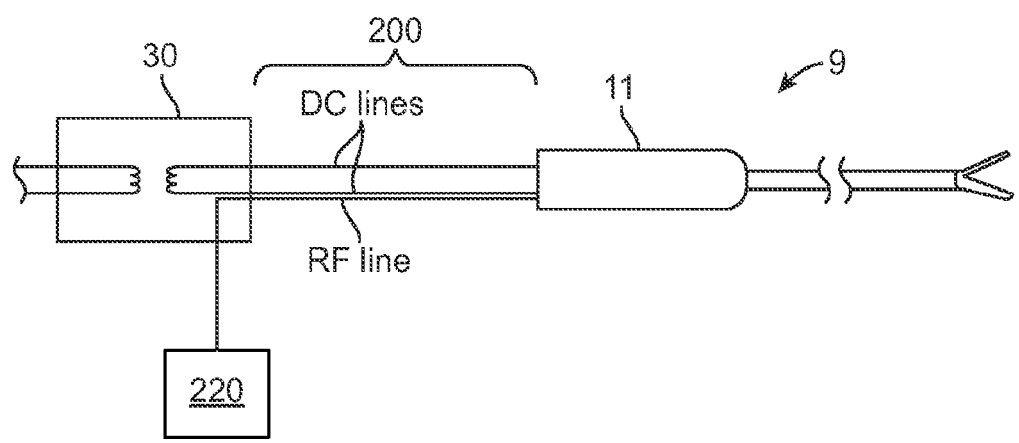
FIG. 12 illustrates a surgical instrument coupled to a DC source and a RF source in accordance with other embodiments.

In the above embodiments, the surgical instrument 9 has been described as having contact terminal(s) for allowing a RF probe to make contact, thereby causing the surgical instrument 9 to deliver RF energy at its distal end. However, in other embodiments, the surgical instrument 9 may be configured to deliver RF energy without using any RF probe to make contact with it. For example, in other embodiments, the surgical instrument 9 may be coupled to the DC source 30 via a cable 200, wherein the cable 200 is for delivering DC energy from the DC source 30 to the surgical instrument 9 (FIG. 12). The cable 200 also includes circuitry for receiving RF energy from a RF source 220 that is coupled to the DC source, as shown in the figure. In one mode of operation, the DC source 30 is configured to transmit DC energy to the surgical instrument 9 via the DC lines 144. In another mode of operation, the DC source 30 is configured to allow RF source 220 to transmit RF energy to the surgical instrument 9 via the RF line 146. The DC source 30 may include a switch for switching between two modes of operation. Alternatively, the switch may be implemented at any point along the length of the cable 200 or at the handle 11. In some cases, a RF control, such as a button, a foot pedal, etc., may be provided, for allowing a user to direct RF energy to the surgical instrument 9. In such cases, after the mode-switch control is activated for allowing delivery of RF energy, RF energy will not be delivered unless the RF control is actuated by the user. This provides a safety feature for preventing accidental delivery of RF energy from the RF source 220. The RF control may be coupled to the RF source 220, to the DC source 30, or at any point along the RF line. In other embodiments, the RF control may also be implemented as a component at the RF source 220, at the DC source 30, or at the cable 200.

Figure 13:
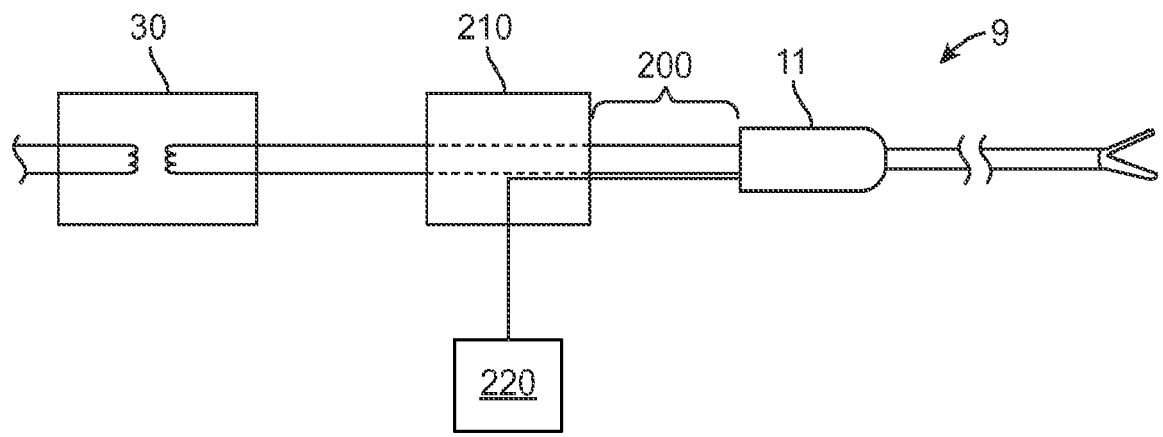
FIG. 13 illustrates a surgical instrument coupled to a DC source and a RF source in accordance with other embodiments.

In other embodiments, the cable 200 may be coupled to a switch box 210. The switch box 210 is configured to receive energy from the DC source 30 and transmit it to the surgical instrument 9 in one mode of operation (FIG. 13). In another mode of operation, the switch box 210 is configured to receive RF energy from a RF source 220, and transmit the RF energy to the surgical instrument 9. The switch box 210 may include a control for allowing a user to switch between the first and second modes of operation. Alternatively, the control for switching between modes of operation may be implemented at any point along the length of the cable 200 or at the handle 11. In some cases, a RF control, such as a button, a foot pedal, etc., may be provided, for allowing a user to direct RF energy to the surgical instrument 9. In such cases, after the switch box 210 is configured to deliver RF energy, RF energy will not be delivered unless the RF control is actuated by the user. This provides a safety feature for preventing accidental delivery of RF energy from the RF source 220. The RF control may be coupled to the RF source 220, the switch box 210, or to any point along the length of the cable 200. In other embodiments, the RF control may also be implemented as a component at the RF source 220, at the switch box 210, or at the cable 200.

As illustrated in the above embodiments, the surgical instrument 9 allows delivery of heat to a remote surgical site for welding and severing vessel, and allows delivery of RF energy for cauterizing tissue to control bleeding. Such an instrument combines a heat delivery function with a RF delivery function to allow a user to address two very different situations (e.g., tissue welding and bleeding control) using a single tool. Also, because many of the components in the surgical instrument 9 that are for providing DC heating are also used for delivering RF energy, operative portion of the surgical instrument 9 maintains a low profile, without any increase in size due to its dual capability. Furthermore, the surgical instrument 9 allows delivery of RF energy in a controlled manner, thereby protecting the vessel being harvested while allowing bleeding to be controlled. Embodiments of the surgical instrument 9 also obviate the need for repeatedly inserting a separate bleeding control device inside the patient to control bleeding, and removing such bleeding control device from the patient, during a vessel harvesting procedure. Thus, embodiments of the surgical instrument 9 described herein allow delivery of RF energy in a way that makes it much easier and more efficient to address bleeding.

Although the above embodiments have been described with reference to the surgical device 14 being a pair of jaws for clamping, cutting, and sealing vessel (e.g., saphenous vein, an artery, or any other vessel), in other embodiments, the surgical device 14 may have different configurations, and different functionalities. For example, in other embodiments, the surgical device 14 may be clip appliers or grasping jaws with no heating functionality, but still include one or more high frequency electrodes for delivering RF energy from RF source to control bleeding. In further embodiments, the bleeding control feature (e.g., the components for allowing RF to be delivered to the distal end of the surgical instrument) may be incorporated in any type of laparoscopic/endoscopic surgical tool, or any type of tool used for open surgery. Also, in any of the embodiments described herein, the surgical instrument 9 may be used in any endoscopic procedure that requires dissection or transection of tissue with bleeding control.

In addition, although the above embodiments have been described with reference to delivering heat energy and RF energy in different times, in other embodiments, the surgical instrument 9 may be configured to deliver heat energy and RF energy simultaneously. For example, in other embodiments, the surgical instrument 9 may include an electrode 40 for delivering heat energy to cut and/or seal tissue, and another electrode for delivering RF energy for bleeding control. In other embodiments, the surgical instrument 9 may include an operative element for simultaneously delivering heat and RF energy.

Also, although the above embodiments have been described with reference to a surgical instrument that has a bleeding control feature, in other embodiments, such bleeding control feature is optional. Thus, in any of the embodiments described herein, the surgical instrument 9 may not include the port(s) 34, the contact terminal(s) 17, and the electrical switch 78. In addition, in any of the embodiments described herein, the jaw assembly at the distal end of the surgical instrument 9 does not need to include all of the features described herein. For example, in some embodiments, the jaw assembly does not include outer electrode portions 50, 52. Instead, the jaw assembly includes one electrode strip (comparable to the middle electrode portion 48 described above) for cutting or sealing tissue. Furthermore, in other embodiments, the jaw 23 may not have the surface elevation 54. Instead, the jaw 23 may have a flat surface that is for contacting the inner and outer electrode portions 48, 50, 52. In addition, in further embodiments, the jaws 21, 23 may not include the respective protrusions 60, 62. Instead, the cross section of the jaw 21/23 may have a symmetrical configuration. In other embodiments, protrusion(s) may be provided on both sides of the jaw assembly (e.g., one or more protrusions at the concave side of the jaw assembly, and one or more protrusions at the convex side of the jaw assembly). Such configuration provides buffering on both sides of the jaw assembly, and allows for correct placement of the jaw assembly regardless of which side (the concave or convex side) of the jaw assembly is oriented towards the main vessel 142 during use. In further embodiments, instead of the curved configuration, the jaws could be straight. Also, in any of the embodiments described herein, instead of, or in addition to, using the electrode 40 for controlling bleeding, the electrode 40 may be used for dissection or transection of tissue, such as fatty and connective tissue encountered during a vessel harvesting procedure.

Although particular embodiments have been shown and described, it will be understood that they are not intended to limit the present inventions, and it will be obvious to those skilled in the art that various changes and modifications may be made without departing from the spirit and scope of the present inventions. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed is:

1. A surgical instrument for harvesting a vessel, comprising:
    an elongated body having a distal end and a proximal end;
    a surgical device at the distal end of the elongated body, wherein the surgical device is configured to operate on a vessel;
    a handle at the proximal end of the elongated body, wherein the handle contains:
        a plurality of connection ports; and
        a resilient electrical contact device that is disposed within the handle, wherein the resilient electrical contact device includes a plurality of resilient contact terminals, wherein each member of the plurality of resilient contact terminals are in an alignment with a respective member of the plurality of connection ports, wherein the alignment is configured to allow an electrosurgical RF probe to access and contact a member of the plurality of resilient contact terminals in order to deliver energy to the surgical device; and
    a control moveably coupled to the handle for operating the surgical device, the control configured to be actuated by one or more fingers;
    wherein the control has a distal portion for operating the surgical device in a first mode of operation, and a proximal portion for operating the surgical device in a second mode of operation, and wherein the distal portion and the proximal portion have different respective configurations for informing a user of the first and second modes of operation, respectively.

2. The surgical instrument of claim 1, wherein the distal portion of the control has a concave configuration, and the proximal portion of the control has a convex configuration.

3. The surgical instrument of claim 1, wherein the distal portion of the control has a first resistance to motion, and the proximal portion of the control has a second resistance to motion that is different from the first resistance to motion.

4. The surgical instrument of claim 1, wherein the surgical device comprises a jaw assembly having a first jaw member and a second jaw member, and the control is moveable for opening and closing the jaw assembly.

5. The surgical instrument of claim 4, wherein the jaw assembly further includes an electrode, and the control is further moveable for controlling a delivery of energy to the electrode.

6. The surgical instrument of claim 1, wherein the surgical device is configured for sealing and cutting the vessel.

7. The surgical instrument of claim 1, further comprising a cable coupled to the handle;
wherein the surgical device comprises an electrode, and wherein the cable has a first wire and a second wire that are electrically coupled to a fuse that connects to the electrode, the second wire being a backup wire for supplying energy to the fuse.

8. The surgical instrument of claim 1, further comprising an electrical switch within the handle, wherein the handle has two wires that are electrically coupled to a switch terminal at the electrical switch, with one of the two wires being a backup wire for supplying energy to the switch terminal.

9. The surgical instrument of claim 1, further comprising an electrical switch within the handle, wherein the control has a first portion located inside the handle for pressing a lever at the electrical switch, and a second portion for providing a tactile feedback to the user of the surgical instrument when the lever at the electrical switch has been pressed.

10. A surgical instrument for harvesting a vessel, comprising:
an elongated body having a distal end and a proximal end;
a surgical device at the distal end of the elongated body, the surgical device configured to operate on a vessel, and having an electrode;
a handle coupled to the proximal end of the elongated body, wherein the handle contains:
a plurality of connection ports; and
a resilient electrical contact device that is disposed within the handle, wherein the resilient electrical contact device includes a plurality of resilient contact terminals, wherein each member of the plurality of resilient contact terminals are in an alignment with a respective member of the plurality of connection ports, wherein the alignment is configured to allow an electrosurgical RF probe to access and contact a member of the plurality of resilient contact terminals in order to deliver energy to the surgical device;
an electrical switch for activating the electrode; and
a control moveably mounted on the handle;
wherein the control comprises a first portion for actuating the electrical switch, and a second portion for providing a tactile feedback to a user of the surgical instrument when the electrical switch has been actuated, and wherein the first and the second portions of the control have an unity construction.

11. The surgical instrument of claim 10, wherein the first portion of the control is configured for pressing a lever at the electrical switch in response to a movement of the control.

12. The surgical instrument of claim 10, wherein the control is asymmetric such that a distal portion of the control and a proximal portion of the control have different respective configurations.

13. The surgical instrument of claim 12, wherein the distal portion of the control has a concave configuration, and the proximal portion of the control has a convex configuration.

14. The surgical instrument of claim 12, wherein the distal portion of the control has a first resistance to motion, and the proximal portion of the control has a second resistance to motion that is different from the first resistance to motion.

15. The surgical instrument of claim 10, wherein the surgical device further comprises a jaw assembly having a first jaw member and a second jaw member, and the control is further moveable for opening and closing the jaw assembly.

16. The surgical instrument of claim 10, wherein the surgical device is configured for sealing and cutting the vessel.

17. The surgical instrument of claim 10, further comprising a cable coupled to the handle;
wherein the cable has a first wire and a second wire that are electrically coupled to the electrode, the second wire being a backup wire for supplying energy to the electrode.

18. The surgical instrument of claim 10, further comprising a cable coupled to the handle; wherein the cable has two wires that are electrically coupled to a switch terminal at the electrical switch, with one of the two wires being a backup wire for supplying energy to the switch terminal.

* * * * *